United States Patent
Van Antwerp et al.

(10) Patent No.: US 9,968,742 B2
(45) Date of Patent: May 15, 2018

(54) COMBINED SENSOR AND INFUSION SET USING SEPARATED SITES

(75) Inventors: Nannette M. Van Antwerp, Valencia, CA (US); Rajiv Shah, Rancho Palos Verdes, CA (US); Bradley J. Enegren, Moorpark, CA (US); Richard Lemos, Jr., Northridge, CA (US); Ly Phou, Los Angeles, CA (US); Garry M. Steil, Pasadena, CA (US); Gayane R. Voskanyan, Glendale, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1195 days.

(21) Appl. No.: 11/897,106

(22) Filed: Aug. 29, 2007

(65) Prior Publication Data
US 2009/0062767 A1 Mar. 5, 2009

(51) Int. Cl.
*A61M 5/172* (2006.01)
*A61B 5/145* (2006.01)
(Continued)

(52) U.S. Cl.
CPC .......... *A61M 5/1723* (2013.01); *A61B 5/1473* (2013.01); *A61B 5/14503* (2013.01);
(Continued)

(58) Field of Classification Search
CPC ............ A61B 5/14503; A61B 5/14532; A61B 5/14546; A61B 5/1473; A61B 5/4839;
(Continued)

(56) References Cited

U.S. PATENT DOCUMENTS

| | | |
|---|---|---|
| 4,402,819 A | 9/1983 | Rechnitz et al. |
| 4,431,004 A | 2/1984 | Bessman et al. |

(Continued)

FOREIGN PATENT DOCUMENTS

| | | |
|---|---|---|
| EP | 0980687 | 2/2000 |
| EP | 1413245 | 4/2004 |

(Continued)

OTHER PUBLICATIONS

International Search Report dated Mar. 12, 2008, International application No. PCT/US2008/074187, International filing date Aug. 25, 2008.

(Continued)

*Primary Examiner* — Shefali Patel
(74) *Attorney, Agent, or Firm* — Gates & Cooper LLP

(57) ABSTRACT

Embodiments of the invention provide a dual insertion set for supplying a fluid to a body of a patient and for monitoring a body characteristic of the patient. Typical embodiments of the invention include a base, an infusion portion coupled to a first piercing member and a sensor portion coupled to a second piercing member. The infusion portion includes a cannula coupled to the first piercing member for supplying the fluid to a placement site. The sensor portion includes a sensor coupled to and extending from the base having at least one sensor electrode formed on a substrate and is coupled to the second piercing member in a manner that allows the sensor to be inserted at the placement site. The base is arranged to secure the dual insertion set to skin of the patient. Typically the first and second piercing members are arranged such that when the first and second piercing members are operatively coupled to the base, they are disposed in a spatial orientation designed to inhibit sensor interference that may be caused by compounds present in fluids infused through the cannula.

5 Claims, 10 Drawing Sheets

(51) Int. Cl.
  *A61B 5/1473* (2006.01)
  *A61B 5/00* (2006.01)
  *A61M 5/142* (2006.01)
  *A61M 5/158* (2006.01)
  *A61B 5/1486* (2006.01)

(52) U.S. Cl.
  CPC ...... *A61B 5/14532* (2013.01); *A61B 5/14546* (2013.01); *A61B 5/4839* (2013.01); *A61B 5/6846* (2013.01); *A61B 5/6848* (2013.01); *A61B 5/6849* (2013.01); *A61M 5/14248* (2013.01); *A61M 5/158* (2013.01); *A61M 5/172* (2013.01); *A61B 5/0031* (2013.01); *A61B 5/1486* (2013.01); *A61M 2005/14252* (2013.01); *A61M 2005/1585* (2013.01); *A61M 2005/1586* (2013.01); *A61M 2005/1587* (2013.01); *A61M 2005/1726* (2013.01); *A61M 2230/201* (2013.01)

(58) Field of Classification Search
  CPC ... A61B 5/6846; A61B 5/6848; A61B 5/6849; A61M 5/14248; A61M 2005/14252; A61M 5/158; A61M 2005/1585; A61M 2005/1586; A61M 2005/1587; A61M 2005/1588; A61M 5/172; A61M 5/1723; A61M 2005/1726; A61M 2230/201
  USPC ....... 604/164.01, 164.07, 264, 272, 48, 500, 604/503, 504, 506, 507, 508, 65, 66, 67, 604/93.01
  See application file for complete search history.

(56) References Cited

U.S. PATENT DOCUMENTS

| | | | |
|---|---|---|---|
| 4,536,274 A | 8/1985 | Papadakis et al. | |
| 4,562,751 A | 1/1986 | Nason et al. | |
| 4,571,292 A | 2/1986 | Liu et al. | |
| 4,573,994 A | 3/1986 | Fischell et al. | |
| 4,678,408 A | 7/1987 | Nason et al. | |
| 4,678,868 A | 7/1987 | Kraska et al. | |
| 4,680,268 A * | 7/1987 | Clark, Jr. ............... | C12Q 1/005 204/403.09 |
| 4,685,903 A | 8/1987 | Cable et al. | |
| 4,703,756 A | 11/1987 | Gough et al. | |
| 4,755,173 A | 7/1988 | Konopka et al. | |
| 4,890,620 A | 1/1990 | Gough | |
| 4,894,253 A | 1/1990 | Heineman et al. | |
| 4,940,858 A | 7/1990 | Taylor et al. | |
| 5,147,781 A | 9/1992 | Rishpon et al. | |
| 5,149,630 A | 9/1992 | Forrest et al. | |
| 5,165,407 A | 11/1992 | Wilson et al. | |
| 5,212,050 A | 5/1993 | Mier et al. | |
| 5,390,671 A | 2/1995 | Lord et al. | |
| 5,390,691 A | 2/1995 | Sproule | |
| 5,391,250 A | 2/1995 | Cheney, II et al. | |
| 5,427,912 A | 6/1995 | Brown et al. | |
| 5,453,185 A | 9/1995 | Frechet et al. | |
| 5,482,473 A | 1/1996 | Lord et al. | |
| 5,494,562 A | 2/1996 | Maley et al. | |
| 5,505,713 A | 4/1996 | Van Antwerp | |
| 5,568,806 A | 10/1996 | Cheney, II et al. | |
| 5,586,553 A | 12/1996 | Halili et al. | |
| 5,605,152 A | 2/1997 | Slate et al. | |
| 5,705,399 A | 1/1998 | Larue | |
| 5,771,868 A | 6/1998 | Khair | |
| 5,777,060 A | 7/1998 | Van Antwerp | |
| 5,786,439 A | 7/1998 | Van Antwerp | |
| 5,800,420 A * | 9/1998 | Gross ............... | A61K 9/0021 204/280 |
| 5,851,197 A | 12/1998 | Marano et al. | |
| 5,882,494 A | 3/1999 | Van Antwerp | |
| 5,968,011 A | 10/1999 | Larsen et al. | |
| 5,981,203 A | 11/1999 | Meyerhoff et al. | |
| 5,985,129 A | 11/1999 | Gough et al. | |
| 6,001,067 A | 12/1999 | Shults et al. | |
| 6,017,328 A | 1/2000 | Fischell et al. | |
| 6,086,575 A | 7/2000 | Mejslov | |
| 6,093,172 A | 7/2000 | Funderburk et al. | |
| 6,119,028 A | 9/2000 | Schulman et al. | |
| 6,120,676 A | 9/2000 | Heller et al. | |
| 6,122,536 A | 9/2000 | Sun et al. | |
| 6,141,573 A | 10/2000 | Kurnik et al. | |
| 6,155,992 A | 12/2000 | Henning et al. | |
| 6,212,416 B1 | 4/2001 | Ward et al. | |
| 6,293,925 B1 | 9/2001 | Safabash et al. | |
| 6,319,540 B1 | 11/2001 | Van Antwerp et al. | |
| 6,368,274 B1 | 4/2002 | Van Antwerp et al. | |
| 6,400,974 B1 | 6/2002 | Lesho | |
| 6,410,251 B2 | 6/2002 | Hoshino et al. | |
| 6,413,393 B1 | 7/2002 | Van Antwerp et al. | |
| 6,461,329 B1 | 10/2002 | Van Antwerp et al. | |
| 6,472,122 B1 | 10/2002 | Schulman et al. | |
| 6,475,196 B1 | 11/2002 | Vachon | |
| 6,484,045 B1 | 11/2002 | Holker et al. | |
| 6,512,939 B1 | 1/2003 | Colvin et al. | |
| 6,514,718 B2 | 2/2003 | Heller et al. | |
| 6,542,765 B1 | 4/2003 | Guy et al. | |
| 6,551,276 B1 | 4/2003 | Mann et al. | |
| 6,554,798 B1 | 4/2003 | Mann et al. | |
| 6,558,351 B1 | 5/2003 | Steil et al. | |
| 6,595,919 B2 | 7/2003 | Berner et al. | |
| 6,607,509 B2 | 8/2003 | Bobroff et al. | |
| 6,702,857 B2 | 3/2004 | Brauker et al. | |
| 6,703,210 B2 | 3/2004 | Egashira | |
| 6,706,159 B2 | 3/2004 | Moerman et al. | |
| 6,736,797 B1 | 5/2004 | Larsen et al. | |
| 6,770,729 B2 | 8/2004 | Van Antwerp | |
| 6,809,653 B1 * | 10/2004 | Mann ................ | A61B 5/0002 340/870.28 |
| 2001/0053891 A1 | 12/2001 | Ackley | |
| 2002/0032374 A1 | 3/2002 | Holker et al. | |
| 2002/0058906 A1 * | 5/2002 | Lebel ................ | A61N 1/37211 604/65 |
| 2002/0090738 A1 | 7/2002 | Cozzette et al. | |
| 2003/0050575 A1 | 3/2003 | Diermann et al. | |
| 2003/0199837 A1 | 10/2003 | Vachon | |
| 2003/0208154 A1 | 11/2003 | Close et al. | |
| 2004/0074785 A1 | 4/2004 | Holker et al. | |
| 2005/0107743 A1 * | 5/2005 | Fangrow, Jr. ............ | 604/164.01 |
| 2005/0115832 A1 | 6/2005 | Simpson et al. | |
| 2005/0131346 A1 * | 6/2005 | Douglas ...................... | 604/136 |
| 2006/0253085 A1 | 11/2006 | Geismar et al. | |
| 2006/0253086 A1 * | 11/2006 | Moberg ................ | A61M 5/1413 604/272 |
| 2007/0135698 A1 | 6/2007 | Shah et al. | |
| 2007/0191702 A1 * | 8/2007 | Yodfat et al. ................. | 600/365 |
| 2007/0191771 A1 * | 8/2007 | Moyer ......................... | 604/158 |

FOREIGN PATENT DOCUMENTS

| | | |
|---|---|---|
| EP | 1502613 | 2/2005 |
| EP | 1153571 | 4/2015 |
| JP | 2002536038 | 10/2002 |
| WO | 93/07945 | 4/1993 |
| WO | 2000/018449 | 4/2000 |
| WO | 2000/019887 | 4/2000 |
| WO | 2000/045696 | 8/2000 |
| WO | 01/58348 | 8/2001 |
| WO | 03/022128 | 3/2003 |
| WO | 03/022352 | 3/2003 |
| WO | 03/023388 | 3/2003 |
| WO | 03/023708 | 3/2003 |
| WO | 03/034902 | 5/2003 |
| WO | 03/035117 | 5/2003 |
| WO | 03/035891 | 5/2003 |
| WO | 03/036255 | 5/2003 |
| WO | 03/036310 | 5/2003 |
| WO | 03/074107 | 9/2003 |
| WO | 2004/008956 | 1/2004 |
| WO | 2004/009161 | 1/2004 |
| WO | 04/021877 | 3/2004 |

(56) References Cited

FOREIGN PATENT DOCUMENTS

| WO | 2004/030726 | 4/2004 |
|----|-------------|--------|
| WO | 2006/102412 | 9/2006 |
| WO | 2007010522  | 1/2007 |
| WO | 2007/070486 | 6/2007 |

OTHER PUBLICATIONS

Japanese Office Action (with English Translation) dated Nov. 6, 2012 for Japanese Patent Application No. 2010-523069.
EPO Communication dated Feb. 9, 2012 for EP application No. 08798612.1 filed on Aug. 25, 2008.
Bruckel, et al., "In Vivo Measurement of Subcutaneous Glucose Concentrations with an Enzymatic Glucose Sensor and a Wick Method," Klin. Wochenschr. 67:491-495, 1989.
Choi et al., "Amperometric biosensors employing an insoluble oxidant as an interference-removing agent," Analytical Chimica Acta, 461, 251-260, 2002.
Murakami, T. et al., "A Micro Planar Amperometric Glucose Sensor Using an Isfet as a Reference Electrode", Analytical Letters, 19, 1973-86, 1986.
Pickup, et al., "In Vivo Molecular Sensing in Diabetes Mellitus: An Implantable Glucose Sensor with Direct Electron Transfer," Diabetologia 32:213-217, 1989.
Shichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20, 1988.
Protein Immobilization: Fundamentals and Applications (Bioprocess Technology, vol. 14) by Richard F. Taylor (Editor) Publisher: Marcel Dekker; (Jan. 7, 1991).
Ward et al., "A new Amperometric Glucose Microsensor: in-vitro and Short Term in vivo evaluation", Biosensors and Bioelectronics 17, 181-189, 2002.
Wong, K. et al. "Application of Electroless Nickel Plating in the Semiconductor Microcircuit Industry", Plating and Surface Finishing, 75, 70-76, 1988.
Yao, T. "A Chemically-Modified Enzyme Membrance Electrode as an Amperometric Glucose Sensor", Analytica Chim. Acta, 148, 27-33, 1983.

* cited by examiner

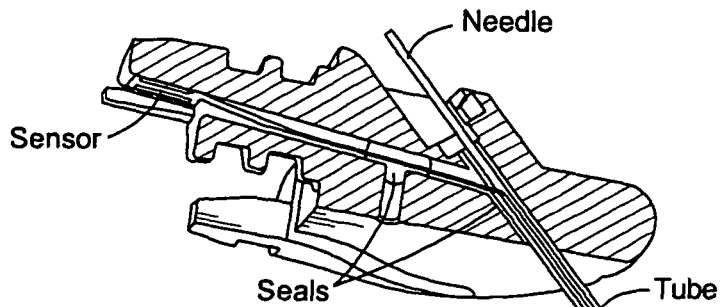
FIG. 8A
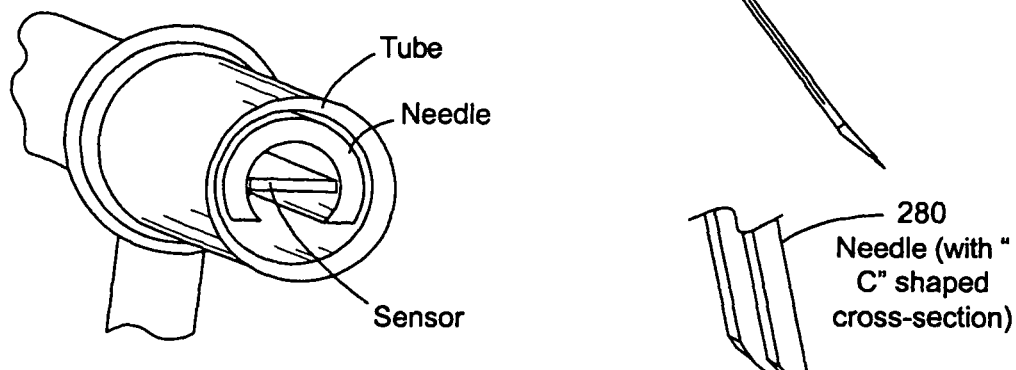
FIG. 8B
FIG. 8C
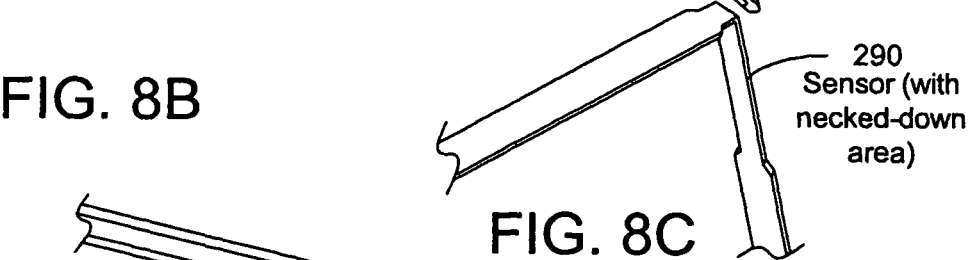
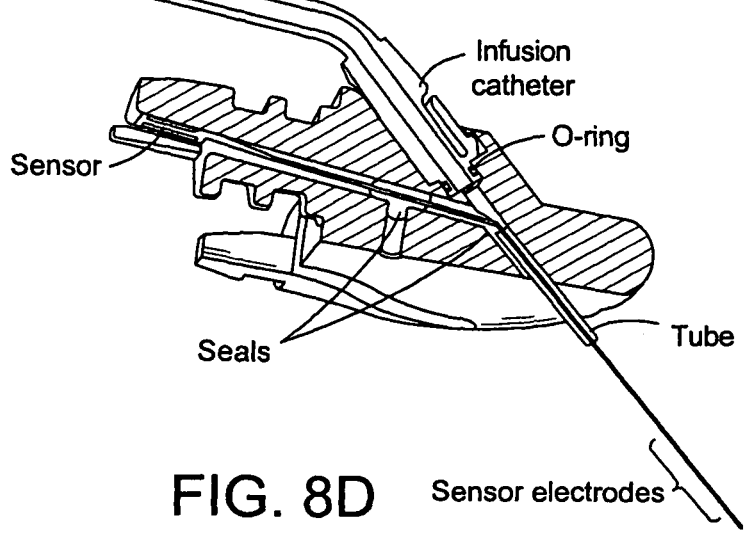
FIG. 8D

COMBINED SENSOR AND INFUSION SET USING SEPARATED SITES

CROSS REFERENCE TO RELATED APPLICATIONS

This application is related to U.S. patent application Ser. No. 10/273,767 filed Oct. 18, 2002 (published as US-2004-0074785-A1), U.S. patent application Ser. No. 10/861,837, filed Jun. 4, 2004, U.S. patent application Ser. No. 11/149,119, filed Jun. 8, 2005, U.S. patent application Ser. No. 11/301,512, filed Dec. 13, 2005, U.S. patent application Ser. No. 11/397,543, filed Apr. 4, 2006, and U.S. patent application Ser. No. 11/492,273, filed Jul. 25, 2006, the contents of each of which are incorporated herein by reference.

BACKGROUND OF THE INVENTION

1. Field of the Invention

Embodiments of the invention relate to apparatuses that combine sensor and infusion elements and to methods for using such apparatuses within the body of a patient.

2. Description of Related Art

Insulin must be provided to people with Type 1 and many with Type 2 diabetes. Traditionally, since it cannot be taken orally, insulin has been injected with a syringe. More recently, use of external infusion pump therapy has been increasing, especially for delivering insulin for diabetics using devices worn on a belt, in a pocket, or the like, with the insulin delivered via a catheter with a percutaneous needle or cannula placed in the subcutaneous tissue. For example, as of 1995, less than 5% of Type 1 diabetics in the United States were using pump therapy. There are now about 12% of the currently over 1,000,000 Type 1 diabetics in the U.S. using insulin pump therapy, and the percentage is now growing at an absolute rate of over 2% each year. Moreover, the number of Type 1 diabetics is growing at 3% or more per year. In addition, growing numbers of insulin using Type 2 diabetics are also using external insulin infusion pumps. Physicians have recognized that continuous infusion provides greater control of a diabetic's condition, and are also increasingly prescribing it for patients. In addition, medication pump therapy is becoming more important for the treatment and control of other medical conditions, such as pulmonary hypertension, HIV and cancer.

Pump therapy systems have been developed that deliver medication by infusion into subcutaneous tissue using an infusion set with needles and/or a soft cannula. The soft cannula of the infusion set is normally inserted into the skin with a needle to prevent kinking of the soft cannula. Automatic insertion devices have been utilized to reduce the discomfort and pain involved with the insertion of infusion sets.

In addition to delivering medication to a patient, a number of other medical devices have been designed to determine body characteristics by obtaining a sample of bodily fluid. A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings can be especially useful in monitoring and/or adjusting a treatment regimen that typically includes the regular administration of insulin to the patient. Thus, blood glucose readings are particularly useful in improving medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, all of which are specifically incorporated by reference herein.

SUMMARY OF THE INVENTION

Embodiments of the invention disclosed herein include apparatuses that combine sensor elements with elements designed to infuse a fluid to a patient in a manner that optimizes a number of sensor characteristics including for example specificity. An illustrative embodiment of the invention is an apparatus for supplying a fluid to a body of a patient (e.g. insulin) and for monitoring a body characteristic of the patient (e.g. blood glucose). The apparatus typically comprises a base adapted to secure the apparatus to the skin of a patient, a first piercing member coupled to and extending from the base and operatively coupled to at least one cannula for infusing a fluid to an infusion site as well as a second piercing member coupled to and extending from the base and operatively coupled to an electrochemical sensor having a sensor electrode for determining at least one body characteristic of the patient at a sensor placement site. In such embodiments of the invention, the first and second piercing members are coupled to the base in an orientation such that when the first and second piercing members can be operatively coupled to the base and inserted into a patient, a first perforation channel made by the first piercing member is not in operable contact with a second perforation channel made by the second piercing member. This embodiment can be used for example to avoid interference of an electrochemical sensor that monitors a body characteristic of a patient, where the interference is caused by a interferant present in an infusate (e.g. a phenolic preservative). In particular, by using an insertable apparatus where a first perforation channel made by the first piercing member is not in operable contact with a second perforation channel made by the second piercing member, a fluid infused to the infusion site (which may contain an interfering species) is prevented from flowing through a perforation channel to the sensor.

In typical embodiments of the invention, the sensor elements and infusion elements (including and their associated piercing members) are positioned on the apparatus in a configuration designed to optimize sensor function. In some embodiments of the invention for example, the first piercing member on the apparatus is shorter than the second piercing member. In certain embodiments of the invention, the first and second piercing members (e.g. metallic needles) are coupled to the base in orientations designed to dispose the infusion site where the fluid exits the cannula in one in vivo environment and the sensor that senses a physiological characteristic in another in vivo environment. In a typical embodiment of the invention, the first and second piercing members are coupled to the base in an orientation such that when the first and second piercing members are inserted into a patient, the infusion site is disposed within a layer of the epidermis and the sensor electrode is disposed within a layer of the dermis. In related embodiments of the invention, the first and second piercing members are coupled to the base in orientations designed to dispose the infusion site where the fluid exits the cannula at a first in vivo location that is placed a certain distance from the in vivo location in which the sensor is disposed. For example, in an illustrative embodiment of the invention, the first and second piercing members are coupled to the base in an orientation such that when the first and second piercing members are inserted into a patient, the infusion site and the sensor electrode are separated by at least 7 millimeters of tissue. By using an insertable apparatus where the infusion site and the sensor are separated by at least 7 millimeters of tissue, a fluid infused to the infusion site (which may contain an interfering species) is absorbed by the surrounding tissue before it can diffuse to the reactive surface of the sensor. In yet another embodiment of the invention, the first and second piercing members are coupled to the base in an orientation so that when the cannula and the sensor electrode are disposed in a patient, the cannula and the sensor electrode anchor the apparatus to the skin of the patient, thereby stabilizing sensor readings, for example by inhibiting movement of sensor in the environment in which it is sensing an analyte.

In certain embodiments of the invention, the apparatus can have a modular design that allows the cannula and/or the sensor to be replaced independently of other components of the apparatus. For example, the apparatuses disclosed herein can include embodiments where the first and second piercing members are disposed on a hub that can operatively engage and disengage from the base. In some embodiments of the invention having a hub, the hub comprises a finger grip member that allows the hub to be gripped as it is disengaged from the base. In some embodiments of the invention, the apparatus can include an array of microneedles for infusing a fluid to an infusion site. Certain embodiments of the invention can include additional elements, for example infusion set tubing adapted to connect to the cannula. Embodiments of the invention can further comprise additional elements designed to facilitate the delivery of a therapeutic composition, for example a medication infusion pump adapted to connect to infusion set tubing.

Another embodiment of the invention is an apparatus for supplying a fluid to a body of a patient and for monitoring a body characteristic of the patient, the apparatus comprising a base adapted to secure the apparatus to the skin of a patient, a piercing member coupled to and extending from the base and having a first and a second lumen, wherein the first lumen comprises an outlet adapted to infuse a fluid to an infusion site, the second lumen comprises an electrochemical sensor disposed therein, wherein the electrochemical sensor comprises a sensor electrode for determining at least one body characteristic of the patient at a sensor placement site and a window that exposes the sensor to the body of the patient; and the outlet of the first lumen and the window of the second lumen are arranged in an orientation such that when the piercing member is operatively coupled to the base and inserted into a patient, an infusate is infused from the orifice at a site that is least 7 millimeters from the window of the second lumen. Optionally in such embodiments, the outlet of the first lumen and the window of the second lumen are arranged in an orientation such that the window of the second lumen is closer to the base than is the outlet of the first lumen. In typical embodiments, the piercing member is a metal needle that is operatively coupled to a catheter that delivers a fluid medication from a fluid reservoir through the outlet of the first lumen to the infusion site. In addition, certain embodiments further comprise infusion set tubing adapted to connect to the cannula and/or a medication infusion pump adapted to connect to the infusion set tubing.

Certain embodiments of the invention are designed for use with specific electrochemical sensor designs. For example in some embodiments of the invention, the sensor portion of the apparatus comprises a plurality of layers, wherein at least one of the layers comprises a base substrate on which the electrode is disposed, the base substrate including a geometric feature selected to increase the surface area of an electrochemically reactive surface on the electrode disposed thereon such that surface area to volume ratio of the electrochemically reactive surface area of the electrode disposed on the geometric feature is greater than surface area-to-volume ratio of the reactive surface of the electrode when disposed on a flat surface, or an analyte sensing layer that detectably alters the electrical current at the electrode in the presence of an analyte, or an adhesion promoting layer that promotes the adhesion between one or more layers of the sensor, or an analyte modulating layer that modulates the diffusion of a analyte therethrough; or a cover layer that is impermeable to blood glucose, wherein the cover layer includes an aperture.

Embodiments of the invention include methods for making and using the apparatuses disclosed herein. One such embodiment of the invention is a method for inhibiting interference of an electrochemical sensor that monitors a body characteristic of a patient, wherein the interference is caused by a interferant present in an infusate (e.g. a phenolic preservative) that is infused by an apparatus for supplying a fluid to a body of a patient, the method comprising supplying a fluid to a body of a patient using an apparatus comprising a base adapted to secure the apparatus to the skin of a patient, a first piercing member coupled to and extending from the base, wherein the first piercing member comprises at least one cannula for infusing a fluid to an infusion site, a second piercing member coupled to and extending from the base and including the electrochemical sensor having a sensor electrode for determining at least one body characteristic of the patient at a sensor placement site, wherein the first and second piercing members are coupled to the base in an orientation such that when the first and second piercing members are inserted into a patient, a first perforation channel made by the first piercing member is not in operable contact with a second perforation channel made by the second piercing member such that a fluid infused to the infusion site cannot flow through the first perforation channel or the second perforation channel to the sensor, so that interference is inhibited.

Embodiments of the invention further include ways to utilize the apparatuses to perform additional and/or multiple methodological functions. For example, in addition to inhibiting interference, certain embodiments of the invention are further designed to stabilize the apparatus by securing it to the patient. One such embodiment of the invention uses an apparatus where the first and second piercing members are coupled to the base in an orientation so that when the cannula and the sensor electrode are disposed in a patient, they function to anchor the apparatus to the skin of the patient. Embodiments of the invention also include those designed for use with certain electrochemical sensor embodiments. In one such embodiment, the method is designed to inhibit interference observed in an electrochemical sensor having a plurality of layers, wherein at least one of the layers comprises a base substrate on which the electrode is disposed, the base substrate including a geometric feature selected to increase the surface area of an electrochemically reactive surface on the electrode disposed thereon such that surface area to volume ratio of the electrochemically reactive surface area of the electrode disposed on the geometric feature is greater than surface area-to-volume ratio of the reactive surface of the electrode when disposed on a flat surface, or an analyte sensing layer that detectably alters the electrical current at the electrode in the presence of an analyte, or an adhesion promoting layer that promotes the adhesion between one or more layers of the sensor, or an analyte modulating layer that modulates the diffusion of a analyte therethrough; or a cover layer that is impermeable to blood glucose, wherein the cover layer includes an aperture.

The invention also provides articles of manufacture such as dual insertion sets including a base, a cannula, piercing member and/or sensor elements, and kits. In one such embodiment of the invention, a kit having an apparatus designed to both infuse a fluid into a patient as well as sensing an analyte as is described above, is provided. The kit and/or sensor set typically comprises a container, a label and an apparatus as described above. The typical embodiment is a kit comprising a container and, within the container, an apparatus having a design as disclosed herein and instructions for using the apparatus.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 5A shows a top view of an apparatus having an assembly with a needle. FIG. 5B shows a bottom view of an apparatus having an assembly with a needle. FIG. 5C shows a cross-section through the sensor/needle port of an apparatus. FIG. 5D shows a cross-section through the infusion port of an apparatus. FIG. 5E shows a cross-section through the sensor/needle port of an apparatus. FIG. 5F shows a bottom-view of an apparatus having an assembly with a sensor needle removed. FIG. 5G shows a cross-section of an apparatus having an assembly with a sensor needle removed. FIG. 5H shows a cross-section view of an apparatus having a microneedle array.

FIG. 6A shows a top view of an apparatus having an assembly with a needle. FIG. 6B shows a bottom view of an apparatus having an assembly with a needle. FIG. 6C shows a cross-section of an apparatus with a needle. FIG. 6D shows a cross-sectional view through the needle/tube/sensor. FIG. 6E shows a view of an apparatus with a catheter. FIG. 6F shows a cross-sectional view of an apparatus with a catheter.

FIG. 7A shows a view of an apparatus having an assembly with a needle. FIG. 7B shows a cross-sectional view of an apparatus having an assembly with a needle. FIG. 7C shows a detailed view of an apparatus assembly with a needle.

FIGS. 8A-8D provide diagrammatic views of embodiments of the invention having a single lumen tube with a protruding sensor and an internal needle. FIG. 8A shows a cross-sectional view of an apparatus having an assembly with a needle. FIG. 8B shows a cross-sectional view through the needle/tube/sensor. a bottom view of an apparatus having an assembly with a needle. FIG. 8C shows a view of needle/sensor engagement. FIG. 8D shows cross-sectional view of an apparatus assembly with a catheter.

DETAILED DESCRIPTION OF THE EMBODIMENTS

Figure 1:
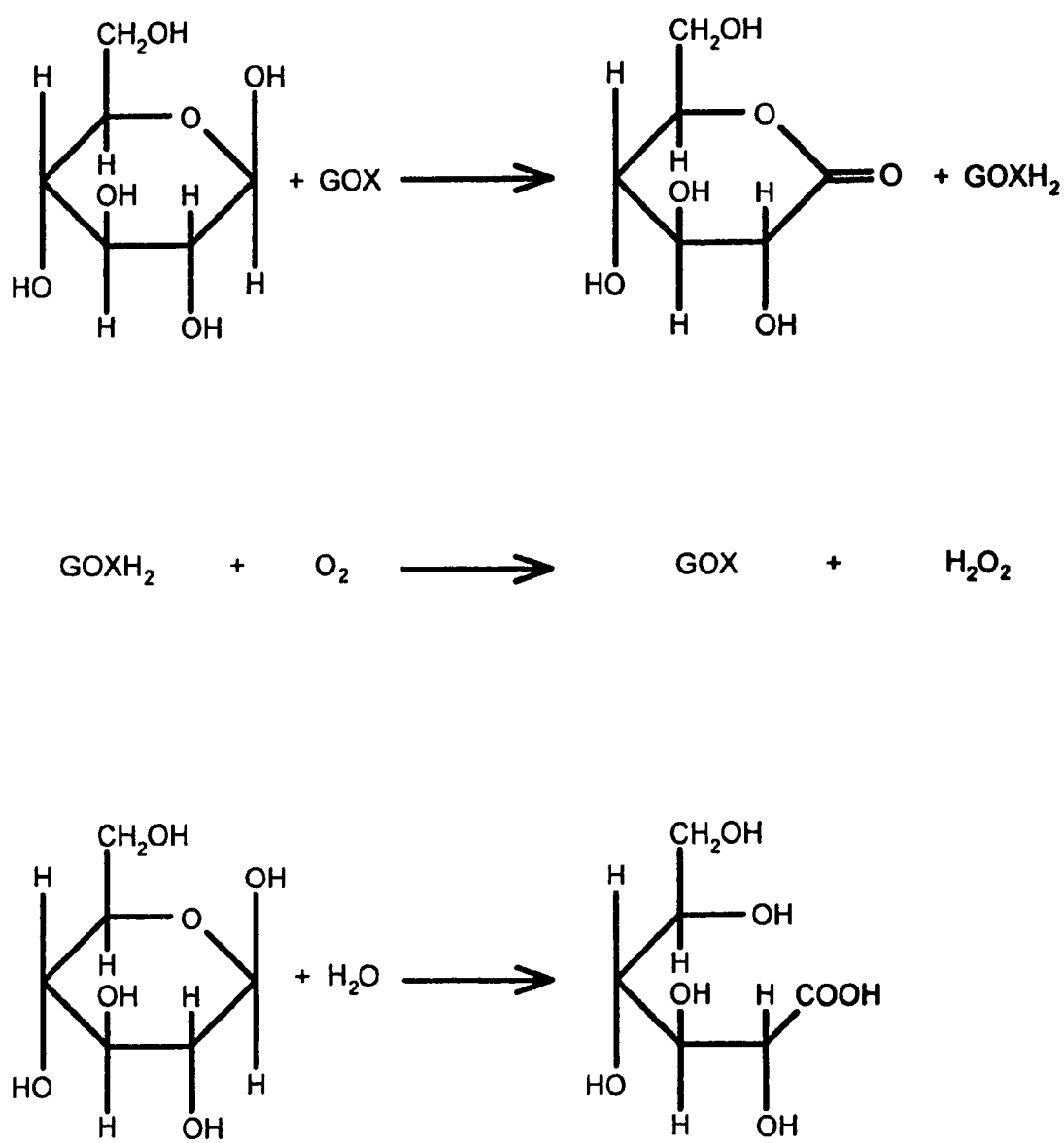
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected reacts creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

The terms "electrical potential" and "potential" as used herein, are broad terms and are used in their ordinary sense, including, without limitation, the electrical potential difference between two points in a circuit which is the cause of the flow of a current. The term "system noise," as used herein, is a broad term and is used in its ordinary sense, including, without limitation, unwanted electronic or diffusion-related noise which can include Gaussian, motion-related, flicker, kinetic, or other white noise, for example.

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. Typically, an "interferant" or "interfering species" is an electroactive compound other than the analyte of interest which, when present in an ionically conductive material, generates a response unrelated to the concentration (or amount) of analyte being measured by the sampling system, thus interfering with the detection of an analyte in the material. In electrochemical sensors, interfering species can be for example compounds with an oxidation potential that overlaps with the analyte to be measured.

The term "phenolic preservative" as used herein refers to art accepted phenolic preservatives that can be used in therapeutic compositions such as chlorocresol, m-cresol, phenol, or mixtures thereof.

As discussed in detail below, embodiments of the invention provide apparatuses that include sensor elements of the type used, for example, in subcutaneous or transcutaneous monitoring of blood glucose levels in a diabetic patient. These apparatuses further include infusion elements such as cannulae of the type used, for example, to infuse insulin into a diabetic patient. In particular embodiments, the invention provides a system for regulating the rate of insulin infusion into the body of a patient based on a glucose concentration measurement taken from the body. In such embodiments, the elements are organized to be spatially separated and further designed to be inserted into proximal yet separate in vivo environments. This organization provides a number of unexpected benefits and for example functions to inhibit sensor interference caused by various compounds present within therapeutic compositions being infused into the body via the infusion elements. Embodiments of the invention may be employed in various infusion environments including, but not limited to biological implant environments. Other environments include, but are not limited to external infusion devices, pumps, or the like.

Embodiments of the invention can include an electrochemical sensor that measures a concentration of an analyte of interest or a substance indicative of the concentration or presence of the analyte in fluid. In some embodiments, the sensor is a continuous device, for example a subcutaneous, transdermal, or intravascular device. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a plurality of layers as discussed in detail below. In typical embodiments, the sensor can use an amperometric, coulometric, conductimetric, and/or potentiometric technique for measuring the analyte.

Embodiments of the invention include an apparatus having a constellation of elements including a sensor element as well as an infusion element so as to provide a dual insertion set, i.e. an apparatus having a base that is operatively coupled to both infusion delivery elements and physiological characteristic sensor elements. In some embodiments, the infusion element of the dual insertion set infuses a fluid, such as a fluid that contains medications, chemicals, enzymes, antigens, hormones, vitamins or the like, into a body of a patient. In particular embodiments of the invention, the dual insertion set may be coupled to an external infusion device, which includes an RF programming capability, a carbohydrate (or bolus) estimation capability and/or vibration alarm capability, as described in U.S. Pat. No. 6,554,798 entitled "External Infusion Device with Remote Programming, Bolus Estimator and/or Vibration Alarm Capabilities," which is specifically incorporated by reference herein. In other embodiments, the dual insertion set may be coupled to other infusion pumps such as the Animas IR-1250, the Deltec Cozmo®, the Disetronic D-Tron® plus, the MiniMed Paradigm®515/715, and the Dana Diabecare® coupled to an external infusion device, the dual insertion set may also include a disconnect cable, allowing the patient to easily disconnect the dual insertion set from the external infusion device to go swimming, take a shower or the like, without having to entirely remove the dual insertion set from the body of the patient. Particular embodiments are directed towards use in humans; however, in alternative embodiments, the dual insertion set may be used in animals.

In certain embodiments, the dual insertion set may be adapted to fit in an insertion tool, as described in U.S. Pat. No. 5,851,197 entitled "Injector For A Subcutaneous Infusion Set," U.S. Pat. No. 6,093,172 entitled "Injector For A Subcutaneous Insertion Set," and U.S. Pat. No. 6,607,509 entitled "Insertion Device For An Insertion Set And Method Of Using The Same," all of which are specifically incorporated by reference herein. The dual insertion may be further adapted for low profile and unobtrusive placement on the patient. In other embodiments, the shape of the dual insertion set may be rectangular, circular, square or the like.

A sensor included in the dual insertion set may be implanted in and/or through subcutaneous, dermal, sub-dermal, inter-peritoneal or peritoneal tissue. In some embodiments of the invention, the sensor may be coupled to a monitor for determining glucose levels in the blood and/or body fluids of the patient without the use of, or necessity of, a wire or cable connection between the transmitter and the monitor. In these embodiments, the sensor utilizes glucose oxidase to determine glucose levels. In still further embodiments, the sensor may use other materials such as optical, fluorescence or electrical materials to determine glucose levels. It will be recognized that further embodiments of the invention may be used to determine the levels of other agents, characteristics or compositions, such as hormones, cholesterol, medication concentrations, pH, oxygen saturation, viral loads (e.g., HIV), or the like. In other embodiments, the sensor may also include the capability to be programmed or calibrated using data received by a telemetered characteristic monitor transmitter device, or may be calibrated at the monitor device (or receiver), as described in U.S. Pat. No. 6,809,653 entitled "Telemetered Characteristic Monitor System And Method Of Using The Same," which is specifically incorporated by reference herein. The telemetered characteristic monitor system may be primarily adapted for use in subcutaneous human tissue. However, still further embodiments may be placed in other types of tissue, such as muscle, lymph, organ tissue, veins, arteries or the like, and used in animal tissue. Embodiments may provide sensor readings on an intermittent, near-continuous and/or continuous basis.

In some embodiments of the invention, the apparatuses of the invention may be coated with medications or other agents that inhibit infection and/or promote healing of the insertion site, as described in U.S. Pat. No. 5,505,713 entitled "Indwelling Catheter With A Stable Enzyme Coating," U.S. Pat. No. 6,475,196 entitled "Subcutaneous Infusion Cannula," U.S. Pat. No. 6,770,729 entitled "Polymer Compositions containing Bioactive Agents and Methods for Their Use," and U.S. Patent Application Publication No. 20030199837 entitled "Anti-Inflammatory Biosensor For Reduced Biofouling And Enhanced Sensor Performance," all of which are specifically incorporated by reference herein. Particular embodiments of the dual insertion set are for transcutaneous placement of the dual insertion set in subcutaneous tissue. In still further embodiments, the sensor portion and infusion portion of the dual insertion may be placed at different depths within the body of the patient.

The dual insertion set of the invention may be used to monitor body characteristics of the patient. In one embodiment, the sensor portion of the dual insertion set monitors blood glucose levels and can be used in conjunction with automated and/or semi-automated medication infusion pumps. In additional embodiments, the sensor portion may be used to determine the levels of other agents, characteristics or compositions, such as hormones, cholesterol, medication concentrations, pH, oxygen saturation, viral loads (e.g., HIV), or the like. The infusion portion of the dual insertion set may be used to provide fluids to the body of a patient. In one embodiment, the infusion portion provides insulin to a diabetic patient. In other embodiments, the infusion portion provides medication, chemicals, enzymes, antigens, hormones, vitamins or the like, to the body of the patient.

As discussed below, embodiments of the invention disclosed herein include sensor and infusion elements and arrangements or configurations of these elements selected to produce optimized sensing properties. The disclosure further provides methods for making and using apparatuses having this combination of elements. While some embodiments of the invention pertain to glucose and/or lactate sensors, a variety of the elements disclosed herein (e.g. piercing members having an architectural organization that functions to inhibit an infused fluid from contacting an implanted sensor) can be adapted for use with any one of the wide variety of sensors known in the art. The analyte sensor elements, architectures and methods for making and using these elements that are disclosed herein can be used to establish a variety of layered sensor structures. Such combined sensor and infusion device elements of the invention exhibit a surprising degree of flexibility and versatility, characteristics which allows these embodiments to be adapted and implemented with a wide variety of known infusion and sensor sets, including for example those described in U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 and WO 03/074107, and European Patent Application EP 1153571, the contents of each of which are incorporated herein by reference.

Specific aspects of the invention are discussed in detail in the following sections.

I. Typical Elements, Configurations and Analyte Sensors of the Invention

Currently, when an insulin pump wearer wants to use a subcutaneous glucose sensor, they typically insert and wear two separate disposable sets, one for the sensor and one for the infusion catheter. Embodiments of the apparatus design described herein allows the sensor and infusion catheter to be built into a single set, which greatly improves comfort and convenience for the patient. For example, a combination glucose sensor/insulin infusion reduces both the amount of hardware the patient has to wear on their body and the number of needle sticks required for use. In certain embodiments of the invention, the 3-D architectural configuration of the elements on the apparatus are arranged so that the relative in vivo positioning of the infusion catheter and the sensor in a patient are precisely controlled so as to inhibit the ability of a liquid infused by the cannula (e.g. a therapeutic insulin composition comprising a phenolic preservative) to flow from the site of infusion to the sensor.

A. Optimized Configurations of the Invention

There are a wide variety of embodiments of the present invention. As shown in the drawings for example, embodiments of the invention disclosed herein are embodied in an apparatus (typically a dual insertion set) that functions to both supply fluids to the body of patient (e.g. insulin) as well as to monitor body characteristics of that patient (e.g. blood glucose levels). The apparatus usually includes at least one piercing member, and typically two piercing members, to pierce the skin during insertion. The piercing member(s) may be a metal needle, hollow, solid, half needle (or other fraction) or the like having a diameter in the range of 18 gauge-29 gauge, or the like, or any range there between. In related embodiments, the piercing member(s) may be made out of other materials, such as ceramic, plastic, composites, silicon micro-needles, biodegradable, hydrophilic substances, substances that soften and/or change once in contact with the body and/or bodily fluids, or the like. In other embodiments, the apparatus may include at least three or more piercing members, or alternatively, only one piercing member. In still further embodiments, the piercing member can include and/or be replaced by replace a cannula that remain in the body to deliver fluids. Other embodiments include at least two or more piercing members. The at least piercing member(s) are coupled to and extends from the base so as to facilitate insertion of the at least one cannula and/or the at least one sensor.

Embodiments of the invention disclosed herein include apparatuses that combine elements designed to infuse a fluid to a patient with electrochemical analyte sensor elements in a manner that optimizes a number of sensor characteristics including the specificity of the analyte sensors. An illustrative embodiment of the invention is an apparatus for supplying a fluid to a body of a patient (e.g. insulin) and for monitoring a body characteristic of the patient (e.g. blood glucose), the apparatus comprising a base adapted to secure the apparatus to the skin of a patient, a first piercing member coupled to and extending from the base, wherein the first piercing member is operatively coupled to at least one cannula for infusing a fluid to an infusion site, a second piercing member coupled to and extending from the base and operatively coupled to an electrochemical sensor having a sensor electrode for determining at least one body characteristic of the patient at a sensor placement site. In this embodiment of the invention, the first and second piercing members are coupled to the base in an orientation such that when the first and second piercing members are operatively coupled to the base and inserted into a patient, a first perforation channel (i.e. an in vivo channel created by the piercing member as it is inserted into a tissue) made by the first piercing member is not in operable contact with a second perforation channel made by the second piercing member. By using an apparatus having elements disposed in this type of orientation, when the device is inserted into the body, the perforation channels created by the infusion element(s) and the perforation channel created by the sensor element(s) are separate and not in contact, a structure that thereby avoids the possibility of a fluid infused from the infusion element(s), one which may contain an interfering species, from travelling through perforation channels to access and possibly interfere with the sensor element.

In certain embodiments of the invention, the first and second piercing members (e.g. metallic needles) are coupled to the base in orientations designed to dispose the infusion site where the fluid exits the cannula in one in vivo environment and the sensor in another in vivo environment. For example, in one embodiment of the invention, the first and second piercing members are coupled to the base in an orientation such that when the first and second piercing members are inserted into a patient, the infusion site is disposed within a layer of the epidermis and the sensor electrode is disposed within a layer of the dermis. In related embodiments of the invention, the first and second piercing members are coupled to the base in orientations designed to dispose the infusion site where the fluid exits the cannula at a first in vivo location that is placed a certain distance from the in vivo location in which the sensor is disposed. This distance is selected to be that where the infusion site and the sensor site are far enough apart so that a fluid infused at an infusion site is absorbed by the surrounding tissue before it can access the sensor element. In this context, studies show that in certain embodiments of the invention, a distance of 7 millimeters is a sufficient distance to allow a fluid infused at an infusion site to be absorbed by the surrounding tissue before it can access the sensor element.

The optimal distance between the infusion site and the sensor element may vary for example depending upon where the apparatus is to be placed. The distance between the infusion site and the sensor element that is sufficient to avoid or inhibit sensor interference caused by the presence of an interfering species in an infused composition in each specific situation can be tested using the illustrative methods and apparatuses disclosed herein. Illustrative tests show that a separation of 7 millimeters of tissue is sufficient under typical conditions used to infuse therapeutic compositions. For example, an approximately 200 µl volume of fluid containing an interfering compound can be infused over a period of approximately 5-15 minutes at a site that is separated by 7 millimeters of tissue from the electrode of an electrochemical sensor without sensor function being compromised by contact with an interferent. The exact distance may be altered depending upon factors including the amount of fluid infused, the rate of infusion (e.g. a slower infusion rate will allow the infused composition to be absorbed at the site and not contact a proximal sensor) and the tissue into which the composition is infused. In this context, some embodiments of the invention, the first and second piercing members are coupled to the base in an orientation such that when the first and second piercing members are inserted into a patient, the infusion site and the sensor electrode are separated by at least 4, 5, 6 or 7, 8 or 9 millimeters of tissue. In yet another embodiment of the invention, the first and second piercing members are coupled to the base in an orientation so that when the cannula and the sensor electrode are disposed in a patient, the cannula and the sensor electrode anchor the apparatus to the skin of the patient, thereby stabilizing sensor readings, for example by inhibiting movement of sensor in the environment in which it is sensing an analyte. In particular, by disposing the infusion catheter and the sensor electrode in the tissue relative to each other in a manner results in the apparatus being secured to the skin, this anchoring configuration functions to inhibit movement of sensor in the environment in which it is sensing an analyte, thereby stabilizing the sensor readings by repeatedly obtaining a sample to be tested from the same in vivo environment from which the previous sample was obtained (and not an environment which has shifted due to sensor movement).

Certain embodiments of the invention include methods which use an apparatus designed to exhibit multiple effects. For example, one such embodiment of the invention is a method for inhibiting interference of an electrochemical sensor that monitors a body characteristic of a patient, wherein the interference is caused by a interferant present in an infusate infused by an apparatus for supplying a fluid to a body of a patient. The method comprises supplying a fluid to a body of a patient using an apparatus comprising a base adapted to secure the apparatus to the skin of a patient, a first piercing member coupled to and extending from the base, wherein the first piercing member comprises at least one cannula for infusing a fluid to an infusion site, a second piercing member coupled to and extending from the base and including the electrochemical sensor having a sensor electrode for determining at least one body characteristic of the patient at a sensor placement site. In this embodiment of the invention interference is inhibited by using an apparatus having a organization of elements selected so that the first and second piercing members are coupled to the base in an orientation such that; (1) when the first and second piercing members are inserted into a patient, a first perforation channel made by the first piercing member is not in operable contact with a second perforation channel made by the second piercing member such that a fluid infused to the infusion site cannot flow through the first perforation channel or the second perforation channel to the sensor; (2) the infusion site is disposed within a layer of the epidermis and the sensor electrode is disposed within a layer of the dermis; and (3) the infusion site and the sensor electrode are separated by at least, 4, 5, 6 or 7 millimeters of tissue. Optionally such methods include those where the first and second piercing members are coupled to the base in an orientation so that when the cannula and the sensor electrode are disposed in a patient, the cannula and the sensor electrode anchor the apparatus to the skin of the patient, thereby stabilizing sensor readings.

In some embodiments of the invention, the apparatus is in a modular configuration that allows the cannula and the sensor to be replaced independently of other components of the apparatus. In addition, the apparatuses disclosed herein include embodiments where the first and second piercing members are disposed on a hub that can operatively engage and disengage from the base. In certain embodiments of the invention having a hub, the hub comprises a finger grip member that allows the hub to be gripped as it is disengaged from the base. In some embodiments of the invention, the first piercing member on the apparatus is shorter than the second piercing member. In certain embodiments of the invention, the apparatus includes an array of microneedles for infusing a fluid to an infusion site. Certain embodiments of the invention include additional element, for example infusion set tubing adapted to connect to the cannula. Other embodiments of the invention can further comprise a medication infusion pump adapted to connect to the infusion set tubing.

Certain embodiments of the invention are designed for use with certain sensor configurations. For example, interference believed to be caused by phenolic preservatives present in therapeutic insulin compositions is observed in the electrochemical sensors discussed in detail herein. Consequently, in some embodiments of the invention, the sensor portion of the apparatus comprises a plurality of layers, wherein at least one of the layers comprises a base substrate on which the electrode is disposed, the base substrate including a geometric feature selected to increase the surface area of an electrochemically reactive surface on the electrode disposed thereon such that surface area to volume ratio of the electrochemically reactive surface area of the electrode disposed on the geometric feature is greater than surface area-to-volume ratio of the reactive surface of the electrode when disposed on a flat surface, or an analyte sensing layer that detectably alters the electrical current at the electrode in the presence of an analyte, or an adhesion promoting layer that promotes the adhesion between one or more layers of the sensor, or an analyte modulating layer that modulates the diffusion of a analyte therethrough; or a cover layer that is impermeable to blood glucose, wherein the cover layer includes an aperture. While certain embodiments of the invention are directed to avoiding or inhibiting interference believed to be caused by phenolic preservatives present in therapeutic insulin compositions is observed in the electrochemical sensors discussed in detail herein, the apparatuses and methods disclosed herein can be used to avoid interference observed in a variety of sensors and caused by a wide variety of compounds.

Another distinct embodiment of the invention is an apparatus for supplying a fluid to a body of a patient and for monitoring a body characteristic of the patient, the apparatus comprising a base adapted to secure the apparatus to the skin of a patient, a piercing member coupled to and extending from the base and having a first and a second lumen, wherein the first lumen comprises an outlet adapted to infuse a fluid to an infusion site, the second lumen comprises an electrochemical sensor disposed therein, wherein the electrochemical sensor comprises a sensor electrode for determining at least one body characteristic of the patient at a sensor placement site and a window that exposes the sensor to the body of the patient; and the outlet of the first lumen and the window of the second lumen are arranged in an orientation such that when the piercing member is operatively coupled to the base and inserted into a patient, an infusate is infused from the orifice at a site that is least 7 millimeters from the window of the second lumen. Optionally in such embodiments, the outlet of the first lumen and the window of the second lumen are arranged in an orientation such that the window of the second lumen is closer to the base than is the outlet of the first lumen. In typical embodiments, the piercing member is a metal needle that is operatively coupled to a catheter that delivers a fluid medication from a fluid reservoir through the outlet of the first lumen to the infusion site. In addition, certain embodiments further comprise infusion set tubing adapted to connect to the cannula and/or a medication infusion pump adapted to connect to the infusion set tubing.

One embodiment of the invention is an apparatus comprising a dual insertion set for supplying a fluid to the body of a patient and for monitoring a body characteristic of the patient. The dual insertion set includes a base, an infusion portion, and a sensor portion. The base may be used to secure the dual insertion set to the skin of a patient. The infusion portion typically has at least one cannula for supplying the fluid to an infusion placement site, which is coupled to and extends from the base. The at least one cannula has at least one lumen with a distal end for fluid communication with the placement site and can further include at least one port structure formed near another end of the at least one lumen opposite the distal end. The sensor portion has at least one sensor coupled to and extending from the base having at least one sensor electrode formed on a substrate. The at least one sensor is for determining at least one body characteristic of the patient at a sensor placement site. Certain embodiments of the invention have the infusion portion and the sensor portion spaced a predetermined distance apart from one another (e.g. at least 3, 4, 5, 6, 7, 8, or 9 or more millimeters apart). Additional embodiments include at least two separate piercing members to insert the at least one cannula and the at least one sensor into the body of the patient. Further embodiments have the infusion portion and the sensor portion equal in length. Other embodiments have the length of the sensor portion sized smaller relative to the length of the infusion portion. Still additional embodiments have the length of the infusion portion sized smaller relative to the length of the sensor portion. Particular embodiments provide metal needles as the piercing members.

Certain embodiments of the invention provide a cannula that includes an outer lumen to supply the fluid and an inner lumen to contain the sensor portion. The outer lumen may be sealed off at the distal end and the inner lumen may be open to allow the at least one sensor to protrude out of the inner lumen. In alternate embodiments, the outer lumen may contain the sensor portion and the inner lumen may supply the fluid. In still other embodiments, the cannula may include side-by-side lumens. The at least one cannula typically includes at least one opening for infusing the fluid into the body of the patient. Additionally, one piercing member may be used to insert the dual insertion set into the body of the patient. Other embodiments may provide a sensor that includes at least one internal power supply. The internal power supply may further drive a leak detection system. Particular embodiments provide insulin as the infused fluid. In certain embodiments, the monitored body characteristic may be blood glucose.

One embodiment of the invention is a dual insertion set for supplying a fluid to a body of a patient and for monitoring a body characteristic of the patient which includes a base, an infusion portion, a sensor portion and at least two piercing members. The base is used to secure the dual insertion set to the skin of a patient. The infusion portion includes at least one cannula for supplying a fluid to an infusion placement site, which is coupled to and extends from the base. The at least one cannula has at least one lumen with a distal end for fluid communication with the placement site and at least one port structure formed near another end of the at least one lumen opposite the distal end. The sensor portion includes at least one sensor having at least one sensor electrode formed on a substrate. The at least one sensor is for determining at least one body characteristic of the patient at a sensor placement site. The piercing members are coupled to and extends from the base to facilitate insertion of the at least one cannula and the at least one sensor. The at least one cannula may also include at least one opening for infusing the fluid into the body of the patient. The structure, geometry and orientation of the piercing members on the apparatuses of the invention can be precisely controlled so that a liquid infused by the cannula of the apparatus will be absorbed by the body and not flow from the site of infusion to the sensor of the apparatus. In some embodiments, the piercing member is a metal needle and the infused fluid is insulin. In other embodiments, the at least one monitored body characteristic is blood glucose. Additional embodiments may include an internal power supply for the at least one sensor. In further embodiments, the internal power supply may drive a leak detection system.

An alternative embodiment of the invention is a method for avoiding inhibiting or decreasing sensor interference caused by an interfering species present in an infusate (e.g. a phenolic preservative), by using a dual insertion set is for supplying a fluid to a body of a patient and for monitoring a body characteristic of the patient including a base, an infusion portion, a sensor portion and a piercing member. The base is used to secure the dual insertion set to the skin of a patient. The infusion portion includes a piercing member for penetrating the skin of the patient and for supplying a fluid to a placement site. The piercing member is coupled to and extends from the base. Additionally, the piercing member has at least one lumen with a distal end for fluid communication with an infusion placement site and at least one port structure formed near another end of the at least one lumen opposite the distal end. The sensor portion includes at least one sensor coupled to and extending from a piercing member of the base and base having at least one sensor electrode formed on a substrate. The at least one sensor is for determining at least one body characteristic of the patient at a sensor placement site. This method uses an apparatus where the relative position and orientation of the piercing members are precisely controlled so that a liquid infused by the cannula will be absorbed by the body and not flow from the site of infusion to the sensor. In this way, the use of such an apparatus in this method allows one to avoid sensor interference caused by an interfering species present in an infusate. In one illustrative embodiment, the interfering species is a phenolic preservative present in a pharmaceutical composition (e.g. insulin) and the sensor is the multi-layered electrochemical sensor that is discussed in detail below.

Figure 3:
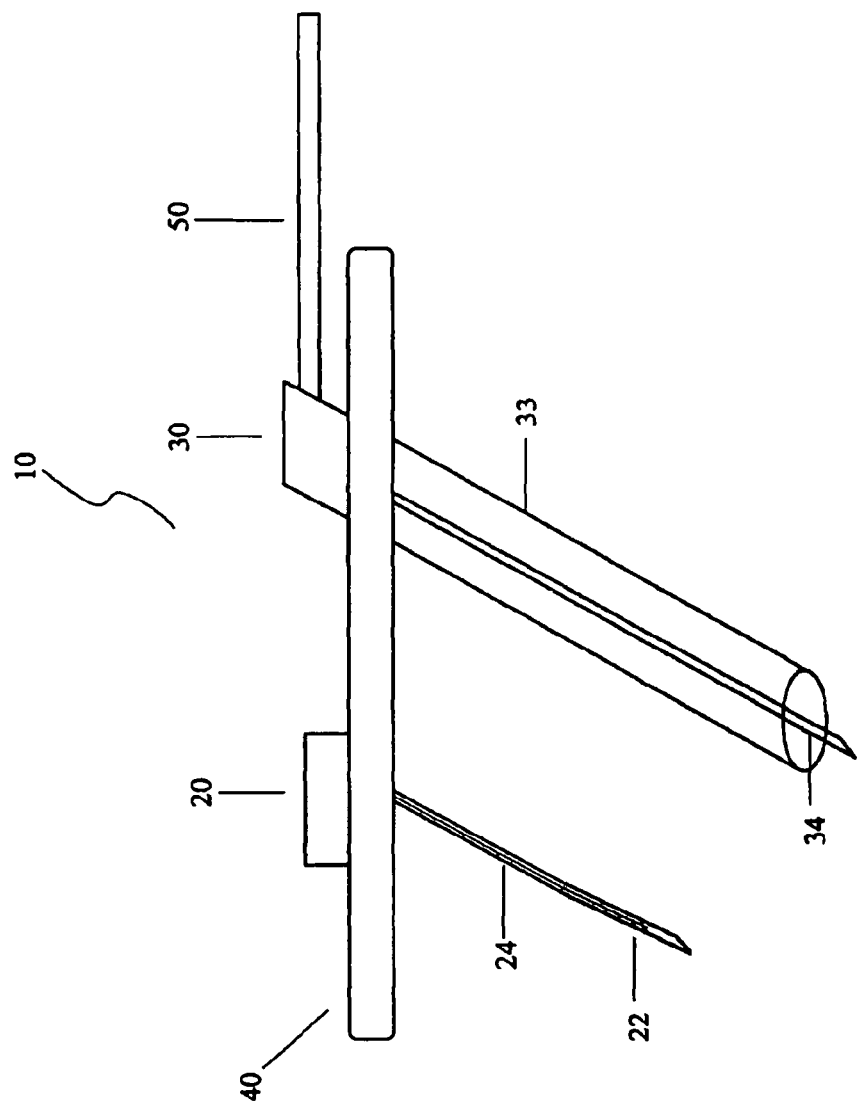
FIG. 3 provides a diagrammatic side view of a dual insertion set embodiment of the invention where a sensor and a cannula are placed at different depths in the body of a patient.
Figure 4A:
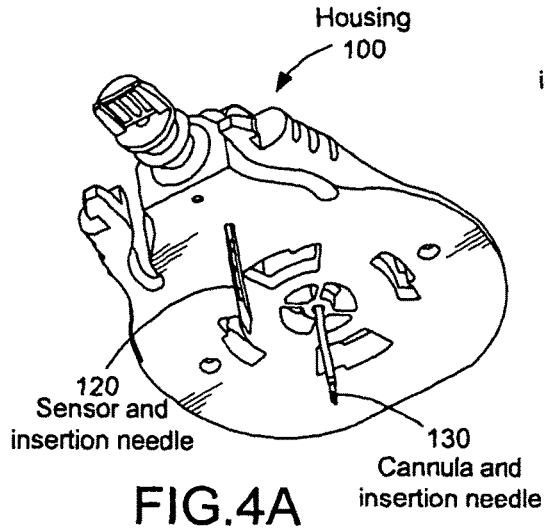
FIGS. 4A-4E provide a diagrammatic view of an embodiment of the invention. In this embodiment, the sensor and sensor connector are built toward one edge of the assembly, while the cannula is positioned toward the center; both are at a 90° angle to the skin surface (FIG. 4A). For insertion, a hub with two needles attached is engagable with the assembly (FIG. 4B). The set is then inserted into the subcutaneous tissue, either manually or with an automatic insertion device. The hub with needles is then removed and discarded. The infusion catheter can then be the attached and the sensor is plugged into a cable or transmitter (FIGS. 4C and 4D). Alternative embodiments can include for example variations where two or more infusion cannulae can be used to further reduce any interference or localized tissue effects (FIG. 4E).
Figure 4B:
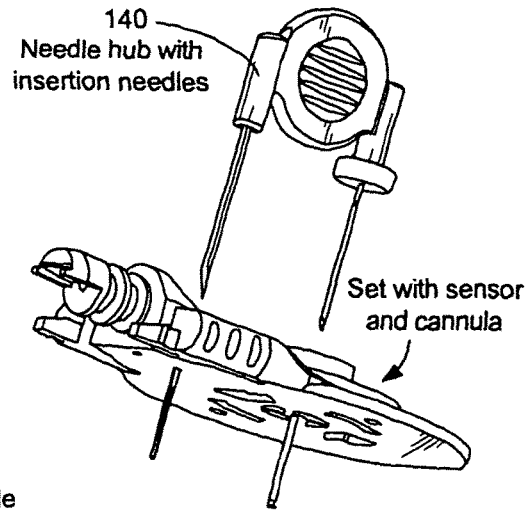
Figure 4C:
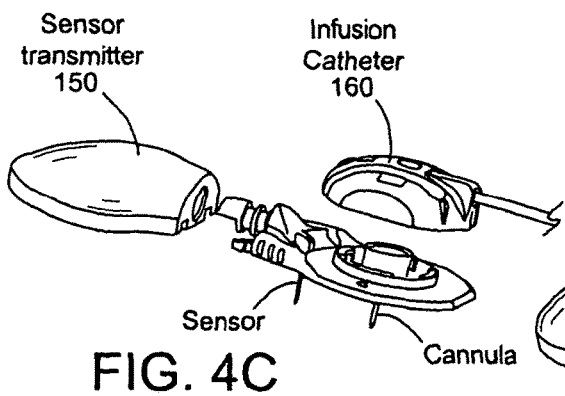
Figure 4D:
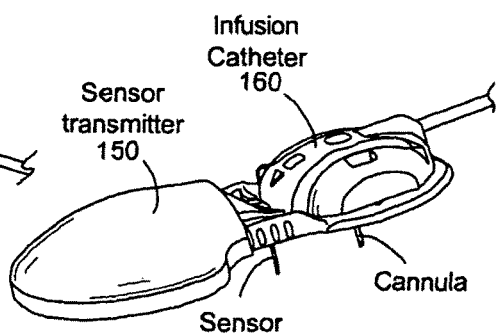
Figure 4E:
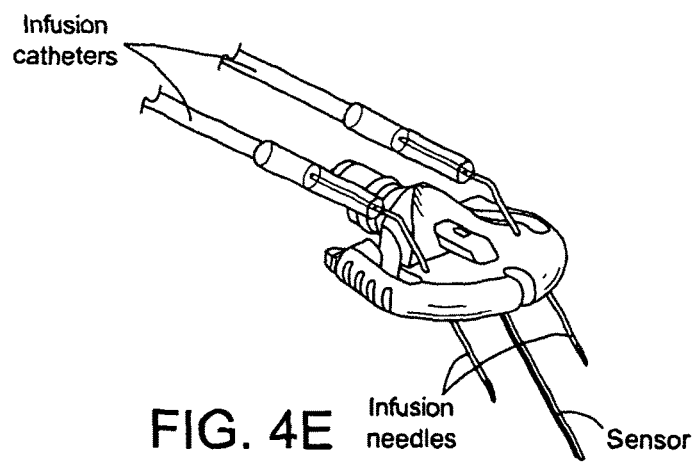
Figure 5A:
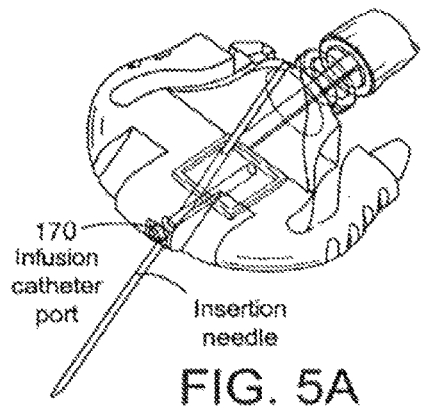
FIGS. 5A-5H provide diagrammatic views of embodiments of the invention.
Figure 5B:
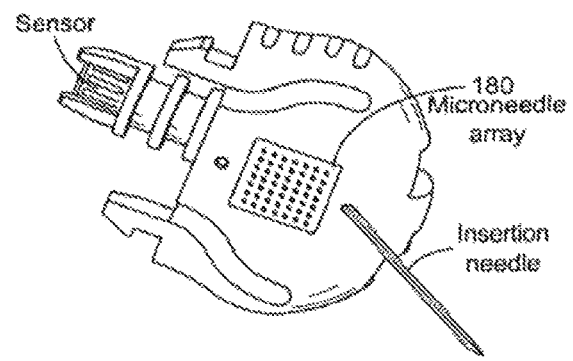
Figure 5C:
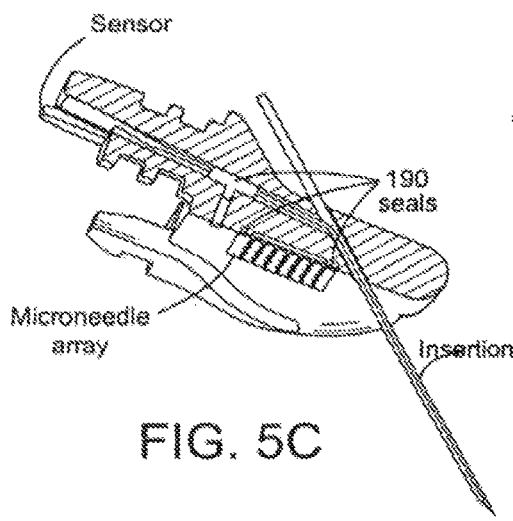
Figure 5D:
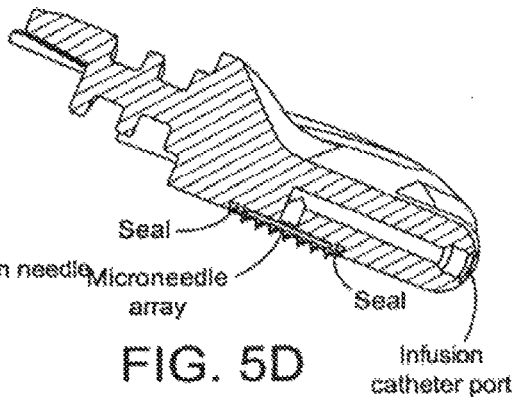
Figure 5E:
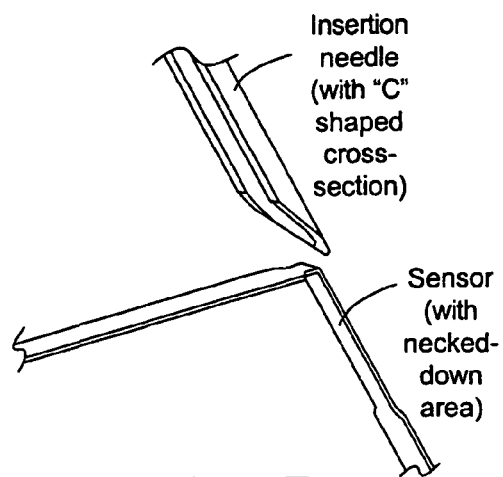
Figure 5F:
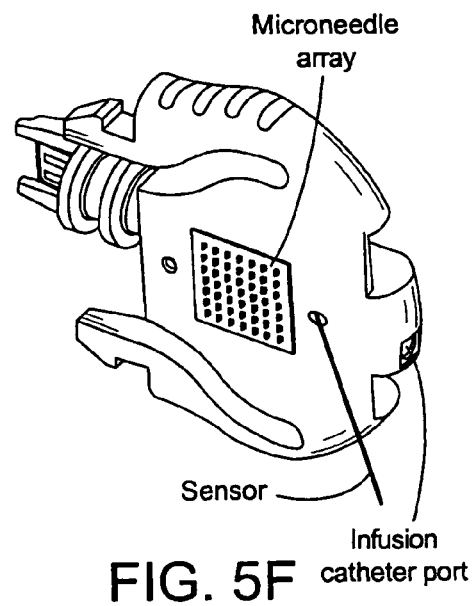
Figure 5G:
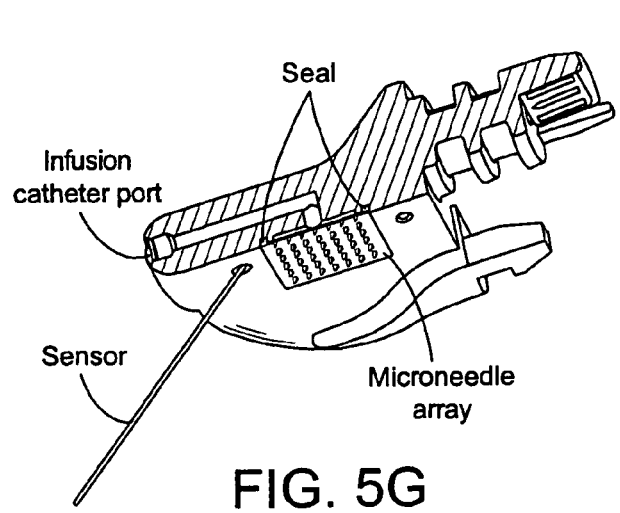
Figure 5H:
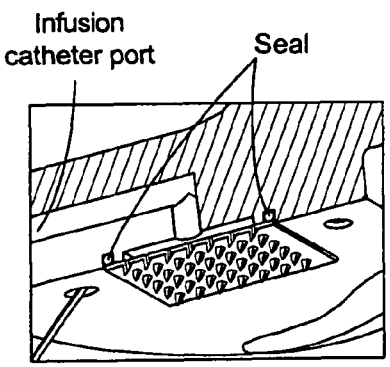
Figure 6A:
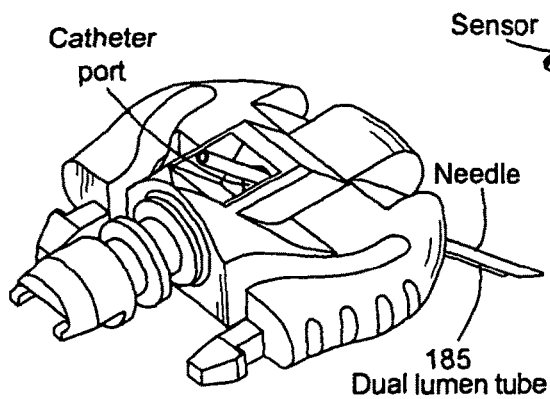
FIGS. 6A-6F provide diagrammatic views of embodiments of the invention having a dual lumen tube.
Figure 6B:
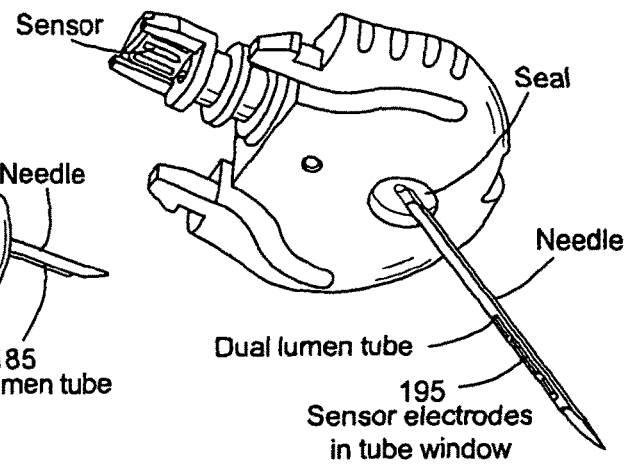
Figure 6C:
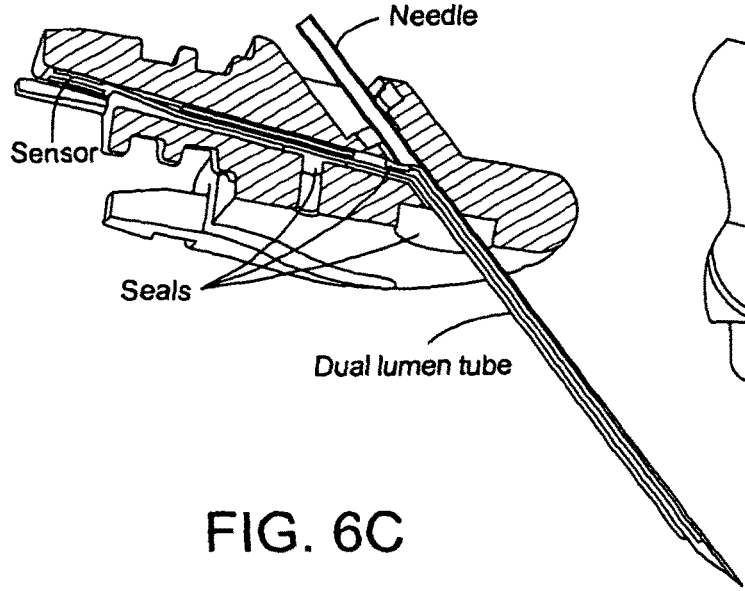
Figure 6D:
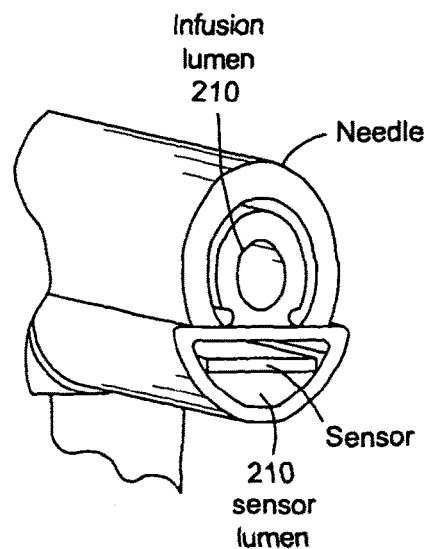
Figure 6E:
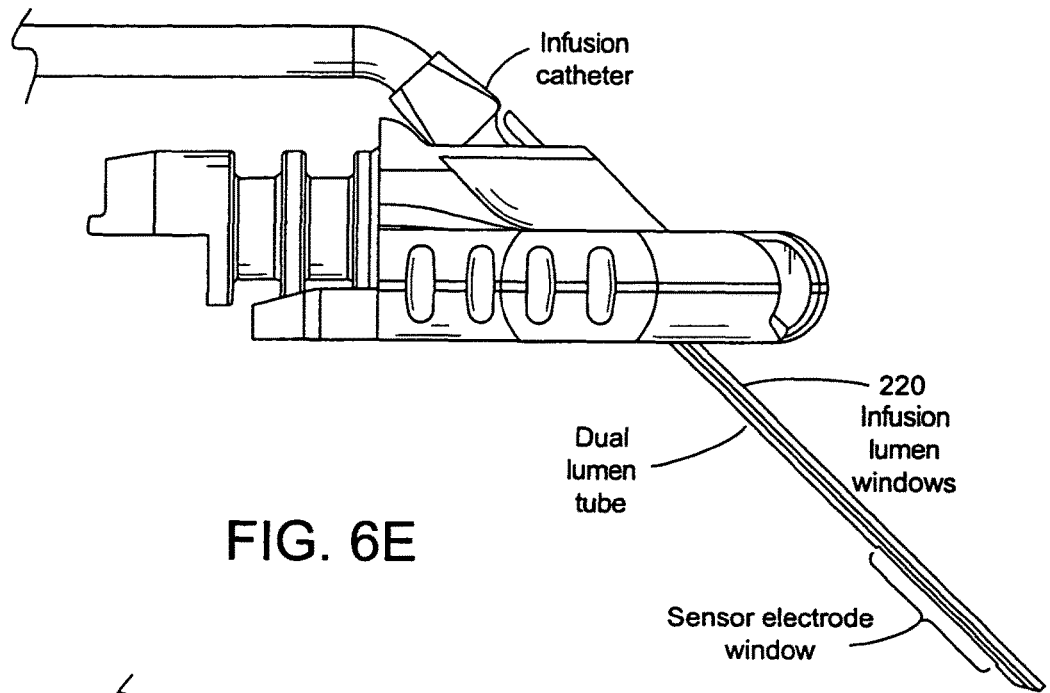
Figure 6F:
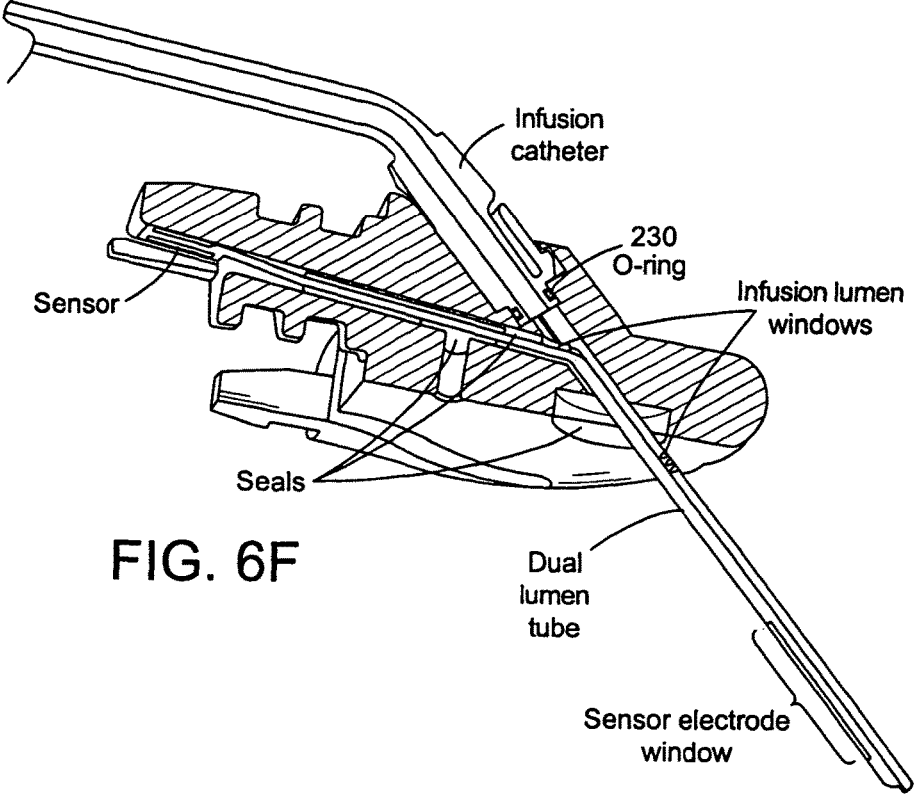

Referring now to the figures, as illustrated in FIG. 3, an apparatus comprising a dual insertion set 10 in accordance with an embodiment of the present invention includes a sensor portion 20, an infusion portion 30, a base 40, a sensor 22, a cannula 33, and piercing members 24 and 34. Both portions 20 and 30 of the dual insertion set 10 are secured to base 40. Infusion portion 30 is connected at one end to tubing 50 that is connected to an external infusion device, pump or the like. The sensor portion 20 is particularly designed for facilitating accurate placement of a sensor, i.e., a flexible thin film electrochemical sensor of the type used for monitoring specific blood parameters representative of a patient condition, as described in U.S. Pat. No. 5,391,250 entitled "Method of Fabricating Thin Film Sensors" and U.S. Pat. No. 6,484,046 entitled "Electrochemical Analyte Sensor," both of which are specifically incorporated by reference herein. In some embodiments, the sensor portion 20 is used to monitor blood glucose levels in diabetic patients as described in U.S. Pat. Nos. 5,390,671, 5,568,806 and 5,586,553, entitled "Transcutaneous Sensor Insertion Set," all of which are specifically incorporated by reference herein.

Figure 7A:
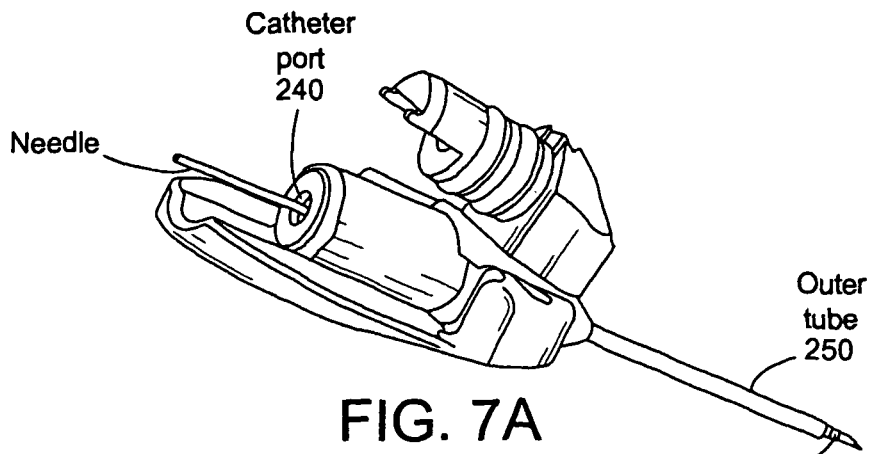
FIGS. 7A-7C provide diagrammatic views of embodiments of the invention having concentric tubes and an internal needle.
Figure 7B:
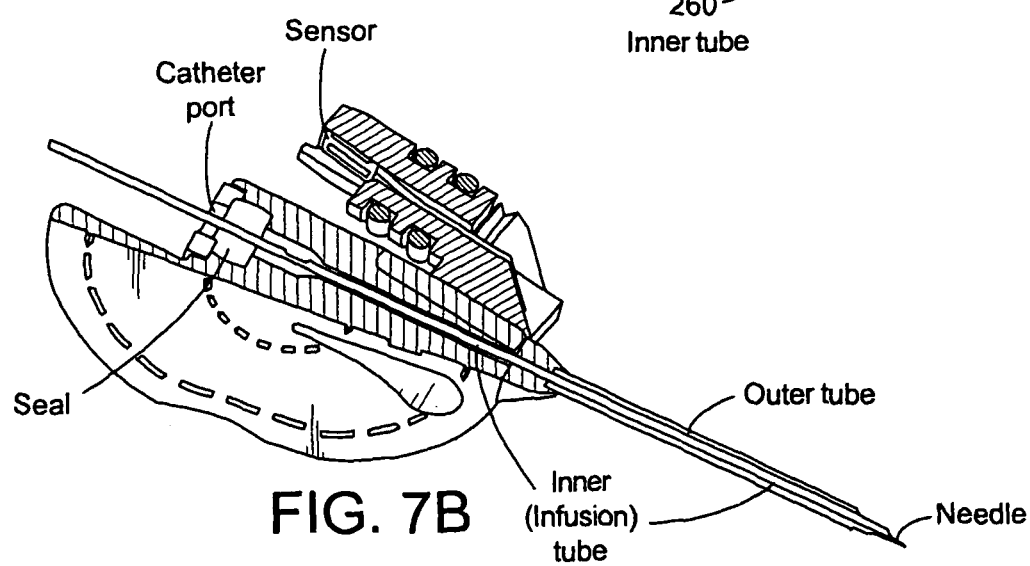
Figure 7C:
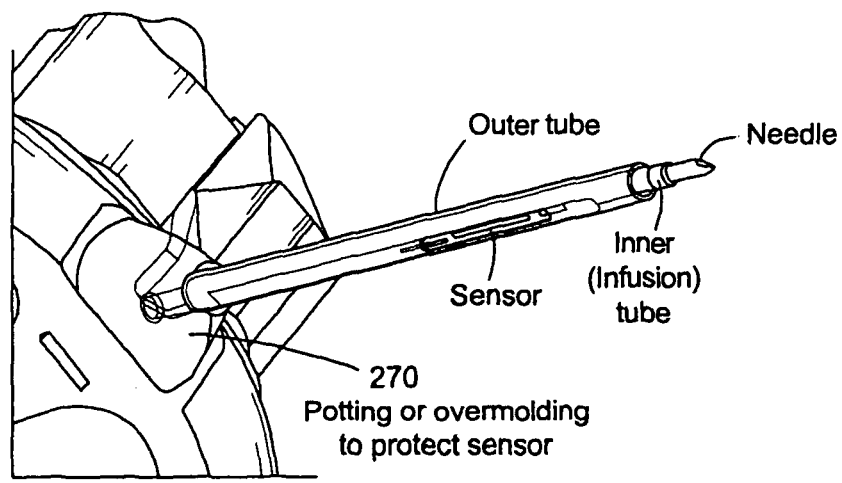

As illustrated by the figures, embodiments of the apparatuses disclosed herein can be adapted for use with a variety of elements. Embodiments shown in FIG. 4 for example include elements such as a base or housing 100, elements comprising a combination of a sensor and insertion needle 120 or a cannula and insertion needle 130, a hub with insertion needles 140 (the hub having a finger grip member that allows the hub to be gripped as it is disengaged from the base), a sensor transmitter 150 and an infusion catheter 160. Embodiments shown in FIG. 5 for example include elements such as an infusion catheter port 170, a microneedle array 180, a microneedle array and various seals 190. Embodiments shown in FIG. 6 for example include elements such as a dual lumen tube 185, a sensor electrode window 195, an infusion lumen 200, a sensor lumen 210, sensor infusion window 220 and o-ring seals 230. Embodiments shown in FIG. 7 for example include elements such as a catheter port 240, an inner tube 250, an outer tube 250 and a potting or overmolding to protect the sensor 270. Embodiments shown in FIG. 8 for example include elements such as a needle with a C-shaped cross-section 280 and a sensor with a necked-down element 290.

Embodiments of this apparatus include those that comprise a subcutaneous sensor and a drug infusion catheter into a single housing, but allows them to be inserted into the skin so that they are spatially separated and/or are disposed in vivo a predetermined 3-D configuration. This separation and/or configuration is designed to diminish interference effects that interfering species in an infusate might have on the sensor itself. In addition, this configuration also may reduce sensor responses to local physiological (or metabolic) effects caused by the infusate. In some embodiments of the invention, the sensor and catheter are inserted into the subcutaneous tissue at a fixed distance apart, for example one where the site of infusion is at least 3, 4, 5, 6, or 7 millimeters from the sensor electrode in an electrochemical sensor. In addition to inhibiting contact between an infusate (e.g. one containing a compound that may interfere with sensor performance) and a sensor electrode, having two separate sites also improves the stability of the device placement in subcutaneous tissue, for example by inhibiting its dislodging from the skin.

In certain embodiments of the invention, an optimum depth for each of the infusion site and the sensor are independently selected and the configuration of the elements arranged accordingly. For example one embodiment of the apparatus includes an arrangement of elements designed to dispose the infusion site in a superficial subcutaneous layer, while disposing the sensor electrode deeper in a layer of the dermis. In particular, the skin includes three distinct layers, a top layer called the epidermis, a middle layer called the dermis and a bottom layer called the subcutaneous layer. The epidermis is about 60 to 120 µm (microns) thick and comprises a number of distinct layers including: a 10 to 20 µm outer layer, called the stratum corneum, followed by the Stratum lucidum and stratum granulosum, stratum spinosum and stratum germinativum (also called "stratum basale"). The stratum corneum contains cells filled with bundles of cross-linked keratin and keratohyalin surrounded by an extracellular matrix of lipids. The inner layers are collectively referred to as the viable epidermis and have a total thickness in the range of about 50 to 100 µm. In certain embodiments of the invention, the apparatus is designed to have a configuration that results in the infusion site and/or the sensor being located in one of these layers.

At the bottom of the epidermis is the basement membrane, which attaches the epidermis firmly, though not rigidly, to the layer below, i.e. the dermis. The dermis is much thicker than the epidermis, having a thickness in the range from about 2,000 to 3,000 µm. The dermal layer generally consists of a dense bed of connective tissue, including collagen fibers, and interstitial fluid dispersed throughout these fibers. The dermis is structurally divided into two areas: a superficial area adjacent to the epidermis, called the papillary region, and a deep thicker area known as the reticular region. The papillary region is composed of loose areolar connective tissue. It is named for its fingerlike projections called papillae, that extend toward the epidermis. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. In certain embodiments of the invention, the apparatus is designed to have a configuration that results in the infusion site and/or the sensor being located in one of these layers or areas.

One exemplary embodiment of an apparatus of the invention is shown in FIG. 4. In this embodiment, the sensor and sensor connector are built toward one edge of the assembly, while the cannula is positioned toward the center; both are at a 90° angle to the skin surface. For insertion, a hub with two needles attached is engaged with the assembly (see, e.g. FIG. 4A). The set is then inserted into the subcutaneous tissue, either manually or with an automatic insertion device. The hub with needles is then removed and discarded (see, e.g. FIG. 4B). The infusion catheter can then be the attached and the sensor is plugged into a cable or transmitter (see, e.g. FIGS. 4C and 4D). Alternative embodiments can include for example variations where: an infusion cannula(e) is made from a rigid material, such as stainless steel, that would not require a separate insertion needle; variations where two or more infusion cannulae can be used to further reduce any interference or localized tissue effects (See, e.g. FIG. 4E); variations where a needle and cannula(e) are built into the set at an angle. In other embodiments, the sensor and infusion components of the set are designed in a modular fashion modular so that either one can be removed and replaced independently of the other.

In another embodiment of the invention, a subcutaneous sensor is combined a microneedles array for drug infusion with in a single disposable set. This embodiment of a combination sensor and infusion set uses a subcutaneous sensor along with a microneedles array for infusion. This arrangement provides for good separation between the sensor electrodes and the infusate to prevent any interference or local tissue effects. One application for this device is a combination glucose sensor/insulin infusion set, but there are other therapies for which this device might prove useful. An embodiment of this type of device is shown in FIG. 5A-5H. In this configuration, the microneedles array is positioned adjacent to the point where the sensor exits the set on the bottom surface of the device. A needle which has one side ground away to form a "C"-shaped cross-section is used to insert the sensor. The insertion needle engages with the sensor via a necked-down area. This allows the needle to protect the sensor during insertion, while still allowing for it to be withdrawn. After insertion, the needle is withdrawn and discarded. The device can be inserted manually or with an automatic insertion device.

Yet another embodiment of the invention is a combination subcutaneous sensor and infusion set using a dual lumen tube. This embodiment of the invention incorporates tubing with two independent lumens to allow a sensor and infusion catheter to share a single site. The sensor is housed in one lumen of the tubing, while the second lumen can be used for infusion. This allows the sensor to be isolated from direct contact with the drug being infused. Typically, the set combines a sensor with an infusion catheter and includes a dual lumen tube that houses the sensor in one lumen while providing a channel for drug infusion through the second lumen. The set can be inserted with a single needle. Relative positions of the windows that provide access to the sensor and an outlet for the drug are optimized depending on desired properties, for example inhibition of sensor contact with potentially interfering species present in an infusate, i.e. configurations that allow for isolation of the sensor electrodes from the flow path of the infusate. For example, the access window for the sensor electrodes can be placed either close to or further away from the infusion lumen windows depending on the optimum relative positions for the given application. One application for this device is a combination glucose sensor/insulin infusion set, but there are other therapeutic contexts for which such devices are useful.

A variety of configurational embodiments for this type of apparatus are shown in FIGS. 6-9. FIGS. 6A-6F shown an embodiment of the invention having a dual lumen tube with external needle. In this embodiment, the needle, which has one side ground away to form a "C"-shaped cross-section, is external to the dual lumen tube. The needle is used to insert the device, then withdrawn and discarded. An infusion catheter can then be plugged into the assembly. An embodiment comprising a dual lumen tube with an internal needle is shown in FIGS. 7A-7F. In this embodiment, the needle resides inside the infusion lumen of the dual lumen tube. The needle is used to insert the device, then withdrawn and discarded. An infusion catheter can then be plugged into the assembly. An embodiment comprising concentric tubes with internal needle is shown in FIGS. 8A-8C. In this embodiment, the sensor resides between the walls of two concentric tubes. The inside diameter of the inner tube houses the insertion needle and also serves as the infusion lumen. The needle is used to insert the device, then withdrawn and discarded. An infusion catheter can then be plugged into the assembly.

Embodiments of the invention include both apparatuses and methods for using these apparatuses in specialized methods, for example those designed to inhibit/avoid sensor interference caused by an interfering substance that is present in an infusate. On such embodiment of the invention is a method for inhibiting interference of an electrochemical sensor that monitors a body characteristic of a patient, wherein the interference is caused by a interferant present in an infusate (e.g. a phenolic preservative) that is infused by an apparatus for supplying a fluid to a body of a patient, the method comprising supplying a fluid to a body of a patient using an apparatus comprising a base adapted to secure the apparatus to the skin of a patient, a first piercing member coupled to and extending from the base, wherein the first piercing member comprises at least one cannula for infusing a fluid to an infusion site, a second piercing member coupled to and extending from the base and including the electrochemical sensor having a sensor electrode for determining at least one body characteristic of the patient at a sensor placement site, wherein the first and second piercing members are coupled to the base in an orientation such that when the first and second piercing members are inserted into a patient, a first perforation channel made by the first piercing member is not in operable contact with a second perforation channel made by the second piercing member such that a fluid infused to the infusion site cannot flow through the first perforation channel or the second perforation channel to the sensor, so that interference is inhibited.

Embodiments of the invention further include those having additional and/or multiple methodological functions. For example, in addition to inhibiting interference, certain embodiments of the invention are further designed to stabilize the apparatus by securing it to the patient. One such embodiment of the invention uses an apparatus where the first and second piercing members are coupled to the base in an orientation so that when the cannula and the sensor electrode are disposed in a patient, they function to anchor the apparatus to the skin of the patient. Embodiments of the invention also include those designed for use with certain sensor embodiments. In one such embodiment, the method is designed to inhibit interference observed in a sensor having a plurality of layers, wherein at least one of the layers comprises a base substrate on which the electrode is disposed, the base substrate including a geometric feature selected to increase the surface area of an electrochemically reactive surface on the electrode disposed thereon such that surface area to volume ratio of the electrochemically reactive surface area of the electrode disposed on the geometric feature is greater than surface area-to-volume ratio of the reactive surface of the electrode when disposed on a flat surface, or an analyte sensing layer that detectably alters the electrical current at the electrode in the presence of an analyte, or an adhesion promoting layer that promotes the adhesion between one or more layers of the sensor, or an analyte modulating layer that modulates the diffusion of a analyte therethrough; or a cover layer that is impermeable to blood glucose, wherein the cover layer includes an aperture.

Yet another embodiment of the invention is a method of making a dual infusion set apparatus for implantation within a mammal comprising the steps of providing a base layer and then disposing an infusion element (or a constellation of infusion elements) on the base and then further disposing a sensor element (or a constellation of sensor elements) on the base to that the apparatus is made. Typically, the 3-D configuration of these elements is controlled during manufacture so as to precisely control the resulting placement of the elements in vivo. Optionally, the sensor element can be made by forming a conductive layer on the base layer, wherein the conductive layer includes a working electrode; forming an analyte sensing layer on the conductive layer, wherein the analyte sensing layer includes a composition that can alter the electrical current at the working electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough and then forming a cover layer disposed on at least a portion of the analyte modulating layer, wherein the cover layer further includes an aperture over at least a portion of the analyte modulating layer.

B. Diagrammatic Illustration of Typical Sensor Configurations

Figure 2:
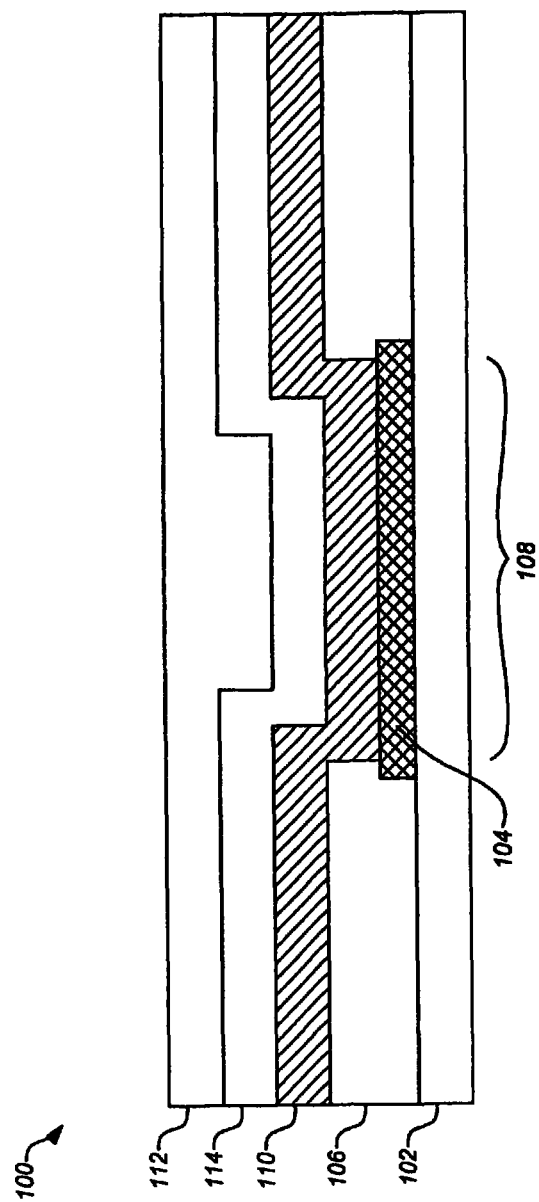
FIG. 2 provides a diagrammatic view of a typical configuration of the sensor element constituents of the current invention.

FIG. 2 illustrates a cross-section of a typical sensor structure 100 of the present invention. The sensor is formed from a plurality of components that are typically in the form of layers of various conductive and non-conductive constituents disposed on each other according to a method of the invention to produce a sensor structure. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. In certain embodiments, the base layer 102 and/or the conductive layer 104 can be constructed to produce electrodes having a configuration where the electrochemically reactive surface area of an electrode is disposed on the geometric feature so that the electrochemically reactive surface area is greater than if it was disposed on a flat surface.

Typically the conductive layer 104 comprises one or more electrodes. An operating sensor 100 typically includes a plurality of electrodes such as a working electrode, a counter electrode and a reference electrode. Other embodiments may also include an electrode that performs multiple functions, for example one that functions as both as a reference and a counter electrode. Still other embodiments may utilize a separate reference element not formed on the sensor. Typically these electrodes are electrically isolated from each other, while situated in close proximity to one another.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating is optionally disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the sensor chemistry layer 110 is an enzyme layer. Most typically, the sensor chemistry layer 110 comprises an enzyme capable of producing and/or utilizing oxygen and/or hydrogen peroxide, for example the enzyme glucose oxidase. Optionally the enzyme in the sensor chemistry layer is combined with a second carrier protein such as human serum albumin, bovine serum albumin or the like. In an illustrative embodiment, an enzyme such as glucose oxidase in the sensor chemistry layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

The analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (µm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include spin coating processes, dip and dry processes, low shear spraying processes, ink-jet printing processes, silk screen processes and the like. Most typically the thin analyte sensing layer 110 is applied using a spin coating process.

Typically, the analyte sensing layer 110 is coated with one or more additional layers. Optionally, the one or more additional layers includes a protein layer 116 disposed upon the analyte sensing layer 110. Typically, the protein layer 116 comprises a protein such as albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art. Typically, the analyte modulating layer comprises a hydrophilic comb-copolymer having a central chain and a plurality of side chains coupled to the central chain, wherein at least one side chain comprises a silicone moiety.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

C. Typical Analyte Sensor Constituents

The following disclosure provides examples of typical elements/constituents used in the sensors of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor).

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as water impermeability and hermeticity. Some materials include metallic ceramic and polymeric substrates or the like. In certain embodiments, the base constituent and/or the conductive constituent can be constructed to produce electrodes having a configuration where the electrochemically reactive surface area of an electrode is disposed on the geometric feature so that the electrochemically reactive surface area is greater than if it was disposed on a flat surface.

The base constituent may be self-supporting or further supported by another material as is known in the art. In one embodiment of the sensor configuration shown in FIG. 2, the base constituent 102 comprises a ceramic. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 25 microns). Alternatively, one can utilize a nonconductive ceramic, such as alumina, in thin constituents, e.g., less than about 25 microns.

Embodiments of invention disclosed herein provide individual elements and sensors which exhibit a combination of the independent advantages found in each of the two sensor classes disclosed above. For example a first embodiment of the invention immobilizes an enzyme onto a thick (1-1,000 micron), porous substrate which functions as an electrode in the sensor. In this context, the porous electrode is designed to exhibit an increased surface area, for example by constructing it from a lattice of equal-sized adjoining spheres. In one illustrative embodiment, glucose oxidase is immobilized on a thick (1-1,000 micron), porous metallic substrate that is manufactured from a lattice of equal-sized adjoining spheres and which function as a hydrogen peroxide-consuming electrode.

In another embodiment of the invention disclosed herein the hydrogel typically utilized in a variety of analyte sensors is replaced with an essentially rigid, non-swelling porous enzyme-polymer matrix. In this embodiment, bio-sensing enzymes can be stably immobilized via covalent bonding to a rigid, macroporous polymer that has optionally been molded into a specified shape. In this context, molded continuous rods of macroporous polymers have been developed for use as chromatographic separation media (see, e.g. U.S. Pat. No. 5,453,185 and WO 93/07945). Suitable polymers are essentially incompressible and do not change their overall size in response to changes in their solvating environment. Moreover, adjustments to the polymerization conditions can be used to control the morphology of the pores. Hence, highly porous (50-70%) polymers can be created that possess significant volume fractions of pores in the ranges of 1-100 nm and 100-3,000 nm (i.e. 20% and 80%, respectively). Polymers with this type of pore structure possess a very high specific surface area (i.e. 185 $m^2/g$), and are expected to allow for high enzyme immobilization densities (1-100 mg/mL).

Various methods and compositions for making and using the above-noted porous matrices as well as analyte sensors which incorporate such matrices are further described herein.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically, for in vivo use the analyte sensors of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Examples of interference rejection constituents include one or more layers or coatings of compounds such as hydrophilic polyurethanes, cellulose acetate (including cellulose acetate incorporating agents such as poly(ethylene glycol), polyethersulfones, polytetrafluoroethylenes, the perfluoronated ionomer Nafion™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference.

Analyte Sensing Constituent

The electrochemical sensors of the invention include an analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent. As discussed for example in U.S. patent application Ser. No. 10/273,767 (incorporated herein by reference) extremely thin sensor chemistry constituents are typical and can be applied to the surface of the electrode matrix by processes known in the art such as spin coating. In an illustrative embodiment, a glucose oxidase/albumin is prepared in a physiological solution (e.g., phosphate buffered saline at neutral pH) with the albumin being present in a range of about 0.5%-10% by weight. Optionally the stabilized glucose oxidase constituent that is formed on the analyte sensing constituent is very thin as compared to those previously described in the art, for example less than 2, 1, 0.5, 0.25 or 0.1 microns in thickness. One illustrative embodiment of the invention utilizes a stabilized glucose oxidase constituent for coating the surface of an electrode wherein the glucose oxidase is mixed with a carrier protein in a fixed ratio within the constituent, and the glucose oxidase and the carrier protein are distributed in a substantially uniform manner throughout the constituent. Typically the constituent is less than 2 microns in thickness. For purposes of clarity, it should be noted that this may not apply to certain embodiments of the invention where the analyte sensing constituent is disposed on a porous electrode. For example, in a porous electrode that is 100 microns thick, with 3 micron size pores that are filled with GOx, an enzyme layer can be greater 2 microns.

Surprisingly, sensors having these extremely thin analyte sensing constituents have material properties that exceed those of sensors having thicker coatings including enhanced longevity, linearity, regularity as well as improved signal to noise ratios. While not being bound by a specific scientific theory, it is believed that sensors having extremely thin analyte sensing constituents have surprisingly enhanced characteristics as compared to those of thicker constituents because in thicker enzyme constituents only a fraction of the reactive enzyme within the constituent is able to access the analyte to be sensed. In sensors utilizing glucose oxidase, the thick coatings produced by electrodeposition may hinder the ability of hydrogen peroxide generated at the reactive interface of a thick enzyme constituent to contact the sensor surface and thereby generate a signal.

As noted above, the enzyme and the second protein are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde, including, but not limited to, an amine reactive, homofunctional, cross-linking reagent such as Disuccinimidyl Suberate (DSS). Another example is 1-Ethyl-3 (3-Dimethylaminopropyl) Carbodiimide (EDC), which is a zero-length cross-linker. EDC forms an amide bond between carboxylic acid and amine groups. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). Typically the GOx concentration is about 115 mg/ml (approximately 22,000 U/ml). In such embodiments, the HSA concentration may vary between about 0.5%-30% (w/v), depending on the GOx concentration. Typically the HSA concentration is about 1-10% w/v, and most typically is about 5% w/v. In alternative embodiments of the invention, collagen or BSA or other structural proteins used in these contexts can be used instead of or in addition to HSA. Although GOx is discussed as an illustrative enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

For embodiments employing enzymes other than GOx, concentrations other than those discussed herein may be utilized. For example, depending on the enzyme employed, concentrations ranging from approximately 10% weight per weight to 70% weight per weight may be suitable. The concentration may be varied not only depending on the particular enzyme being employed, but also depending on the desired properties of the resulting protein matrix. For example, a certain concentration may be utilized if the protein matrix is to be used in a diagnostic capacity while a different concentration may be utilized if certain structural properties are desired. Those skilled in the art will understand that the concentration utilized may be varied through experimentation to determine which concentration (and of which enzyme or protein) may yield the desired result.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. The electron transfer is aided by electron-transfer mediators which can accept electrons from the enzyme and donate them to the electrode or vice versa (e.g. ferrocene) or by electron-transfer promoters which retain the enzyme in close proximity with the electrode without themselves taking up a formal charge. U.S. Pat. No. 5,147,781 (which is incorporated herein by reference) describes an assay for the determination of the enzyme lactate dehydrogenase-5 (LDH5) and to a biosensor for such quantitative determination. The assay is based on the interaction of this enzyme with the substrate lactic acid and nicotine-amine adenine dinucleotide (NAD) to yield pyruvic acid and the reduction product of NAD. Anti-LDH5 antibody is bound to a suitable glassy carbon electrode; this is contacted with the substrate containing LDH5, rinsed, inserted into a NAD solution, connected to an amperometric system, and current changes are measured in the presence of differing concentrations of lactic acid, which are indicative of the quantity of LDH-5. U.S. Pat. No. 6,410,251 (which is incorporated herein by reference) describes an apparatus and method for detecting or assaying one constituting member in a specific binding pair; for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GO$_x$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent includes an agent selected for its ability to crosslink a siloxane moiety present in a proximal constituent such as the analyte modulating constituent. In closely related embodiments of the invention, the adhesion promoting constituent includes an agent selected for its ability to crosslink an amine or carboxyl moiety of a protein present in a proximal constituent such a the analyte sensing constituent and/or the protein constituent.

Analyte Modulating Constituent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

As described in detail herein, in certain embodiments of the invention, the analyte modulating constituent comprises a hydrophilic comb-copolymer having a central chain and a plurality of side chains coupled to the central chain, wherein at least one side chain comprises a silicone moiety.

Cover Constituent

The electrochemical sensors of the invention include one or more cover constituents which are typically electrically insulating protective constituents (see, e.g. element 106 in FIG. 2). Typically, such cover constituents are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Various illustrative embodiments of the invention and their characteristics are discussed in detail in the following sections.

D. Illustrative Embodiments of Analyte Sensor Apparatus and Associated Characteristics The apparatuses that include both infusion elements and analyte sensor elements as disclosed herein has a number of embodiments. A general embodiment of the invention is an apparatus for implantation within a mammal. While the apparatuses are typically designed to be implantable within the body of a mammal, the sensors are not limited to any particular environment and can instead be used in a wide variety of contexts, for example for the analysis of most liquid samples including biological fluids such as wholeblood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, embodiments of the invention disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include, for example, those used to monitor one or more analytes present in one or more physiological environments in a hospitalized patient.

Embodiments of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

In general, the analyte sensor apparatus structure comprises a base layer and a conductive layer disposed upon the base layer (e.g. a porous matrix) and functions as one or more electrodes. For example, the conductive layer can include a working electrode, a reference electrode and/or a counter electrode. These electrodes can be spaced in proximity, or alternatively are spaced distally, according to the specific design. The sensor apparatus design is such that certain electrodes (e.g. the working electrode) can be exposed to the solution containing the analyte to be sensed (e.g. via an aperture) in the sensor apparatus. The sensor apparatus design is such that certain electrodes (e.g. the reference electrode) are not exposed to the solution containing the analyte to be sensed in the sensor apparatus.

One embodiment of the invention is a composition for use in biosensors. Such compositions are typically designed to be implantable within a mammal and comprise a porous matrix having a surface coated with an immobilized enzyme, for example glucose oxidase, glucose dehydrogenase, lactate oxidase, hexokinase or lactate dehydrogenase. Typically the porous matrix coated with an immobilized enzyme is capable of acting as an electrode in an electrochemical sensor. Optionally the electrode in the electrochemical sensor consumes hydrogen peroxide.

The matrices used in various embodiments of the biosensors of the invention can be generated from a variety of materials and can be adapted to a variety of compositional configurations. In some embodiments of the invention, the matrix is porous and comprises a ceramic material and/or a metal and/or a macroporous polymer. Optionally the porous matrix comprises a lattice of particles. Typically the particles are spherical. In typical embodiments of the invention, porous matrix has a surface area that is at least 2, 4, 6, 8, 10, 12, 14, 16 or 18 times the surface area of a non-porous matrix of same dimensions. In certain embodiments of the invention, the porous matrix is at least 1, 10, 100, or 1000 microns thick. In certain embodiments of the invention, the porosity range of the porous matrix is optionally about 5-99.9% and typically is about 40-99%. The porosity of these matrices can be measured by one of the protocols typically used in the art such as mercury or gas porosimetry, size-exclusion chromatography using marker molecules of various sizes and molecular weights (e.g. acetone, various globular proteins of a defined size, blue dextran), and cyclic voltammetry.

Typically, the analyte sensor apparatus includes an analyte sensing layer disposed on a conductive layer of the sensor, typically covering a portion or all of the working electrode. This analyte sensing layer detectably alters the electrical current at the working electrode in the conductive layer in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers comprise an enzyme such as glucose oxidase (e.g. for use in glucose sensors) or lactate oxidase (e.g. for use in lactate sensors). In some embodiments of the invention, the analyte sensing layer is disposed upon a porous metallic and/or ceramic and/or polymeric matrix with this combination of elements functioning as an electrode in the sensor.

Typically, the analyte-sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin, for example, less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings described herein, these thin coatings are typical embodiments of the invention.

In sensors utilizing glucose oxidase for example, the thick coatings produced by electrodeposition may hinder the ability of hydrogen peroxide generated at the reactive interface of the 3-5 micron thick enzyme layer to contact the sensor surface and thereby generate a signal. In addition, hydrogen peroxide that is unable to reach a sensor surface due to such thick coatings can diffuse away from the sensor into the environment in which the sensor is placed, thereby decreasing the sensitivity and/or biocompatibility of such sensors. Moreover, while not being bound by a specific scientific theory, it is believed that sensors having such thin analyte sensing layers have unexpectedly advantageous properties that result from the fact that processes such as spin coating, or the like, allow for a precise control over the enzyme coating's ratio of glucose oxidase to albumin (which is used as a carrier protein to stabilize the glucose oxidase in the enzyme layer). Specifically, because glucose oxidase and albumin have different isoelectric points, electrodeposition processes may result in a surface coating in which an optimally determined ratio of enzyme to carrier protein is detrimentally altered in the electrodeposition process, and further wherein the glucose oxidase and the carrier protein are not distributed in a substantially uniform manner throughout the disposed enzyme layer. In addition, sensors having such thin analyte sensing layers have unexpectedly faster response times. While not being bound by a specific scientific theory, it is believed that these surprising and advantageous properties result from the observation that thin enzyme layers allow better access to the working electrode surface and may allow a greater proportion of the molecules that modulate current at the electrode to access the electrode surface. In this context, in certain sensor embodiments of the invention, an alteration in current in response to exposure to the analyte present in the body of the mammal can be detected via an amperometer within 15, 10, 5 or 2 minutes of the analyte contacting the analyte sensor.

Optionally, the analyte sensing layer has a protein layer disposed thereon and which is typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function and provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as GOx from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly, sensors having such a silane containing adhesion promoting layers exhibit unexpected properties including an enhanced overall stability. In addition, silane containing adhesion promoting layers provide a number of advantageous characteristics in addition to an ability to enhancing sensor stability, and can, for example, play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serve to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. In certain embodiments of the invention, the analyte modulating layer comprises a hydrophilic comb-copolymer having a central chain and a plurality of side chains coupled to the central chain, wherein at least one side chain comprises a silicone moiety.

Typically the analyte modulating layer further comprises one or more cover layers which are typically electrically insulating protective layers disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. An illustrative cover layer comprises spun on silicone. Typically the cover layer further includes an aperture that exposes at least a portion of a sensor layer (e.g. analyte modulating layer) to a solution comprising the analyte to be sensed.

The analyte sensors described herein can be polarized cathodically to detect, for example, changes in current at the working cathode that result from the changes in oxygen concentration proximal to the working cathode that occur as glucose interacts with glucose oxidase as shown in FIG. 1. Alternatively, the analyte sensors described herein can be polarized anodically to detect for example, changes in current at the working anode that result from the changes in hydrogen peroxide concentration proximal to the working anode that occur as glucose interacts with glucose oxidase as shown in FIG. 1. In typical embodiments of the invention, the current at the working electrode(s) is compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

In some embodiments of the invention, the analyte sensor apparatus is designed to function via anodic polarization such that the alteration in current is detected at the anodic working electrode in the conductive layer of the analyte sensor apparatus. Structural design features that can be associated with anodic polarization include designing an appropriate sensor configuration comprising a working electrode which is an anode, a counter electrode which is a cathode and a reference electrode, and then selectively disposing the appropriate analyte sensing layer on the appropriate portion of the surface of the anode within this design configuration. Optionally this anodic polarization structural design includes anodes, cathodes and/or working electrodes having different sized surface areas. For example, this structural design includes features where the working electrode (anode) and/or the coated surface of the working electrode is larger than the counter electrode (cathode) and/or the coated surface of the counter electrode. In this context, the alteration in current that can be detected at the anodic working electrode is then correlated with the concentration of the analyte. In certain illustrative examples of this embodiment of the invention, the working electrode is measuring and utilizing hydrogen peroxide in the oxidation reaction (see e.g. FIG. 1), hydrogen peroxide that is produced by an enzyme such as glucose oxidase or lactate oxidase upon reaction with glucose or lactate respectively. Such embodiments of the invention relating to electrochemical glucose and/or lactate sensors having such hydrogen peroxide recycling capabilities are particularly interesting because the recycling of this molecule reduces the amount of hydrogen peroxide that can escape from the sensor into the environment in which it is placed. In this context, implantable sensors that are designed to reduce the release of tissue irritants such as hydrogen peroxide will have improved biocompatibility profiles. Moreover as it is observed that hydrogen peroxide can react with enzymes such as glucose oxidase and compromise their biological function, such sensors are desired due to their avoidance of this phenomena. Optionally, the analyte modulating layer (e.g. a glucose limiting layer) can include compositions that serve to inhibit the diffusion of hydrogen peroxide out into the environment in which the sensor is placed. Consequently, such embodiments of the invention improve the biocompatibility of sensors that incorporate enzymes that produce hydrogen peroxide by incorporating hydrogen peroxide recycling elements disclosed herein.

Certain embodiments of the analyte sensors of the invention that comprise a base layer, a conductive layer, an analyte sensing layer, an optional protein layer, an adhesion promoting layer, an analyte modulating layer and a cover layer exhibit a number of unexpected properties. For example, in sensors that are structured to function via anodic polarization versus those structured to function via cathodic polarization, differences in the electrochemical reactions in the analyte sensing layer as well as at the electrode surface generate and/or consume different chemical entities, thereby altering the chemical environment in which the various sensor elements function in different polarities. In this context the sensor structure disclosed herein provides a surprisingly versatile device that is shown to function with an unexpected degree of stability under a variety of different chemical and/or electrochemical conditions.

In certain embodiments of the invention disclosed herein (e.g., those having hydrogen peroxide recycling capabilities) the sensor layer has a plurality of electrodes including a working electrode (e.g. an anode) and a counter electrode (e.g. a cathode), both of which are coated with an analyte sensing layer comprising an enzyme such as glucose oxidase or lactate oxidase. Such sensor designs have surprising properties including an enhanced sensitivity. Without being bound by a specific theory, these properties may result from the enhanced oxidation of hydrogen peroxide at the surface of a working or a counter electrode which produces additional oxygen that can be utilized in the glucose sensing reaction (see, e.g., FIG. 1). Therefore this recycling effect may reduce the oxygen dependent limitations of certain sensor embodiments disclosed herein. Moreover, this design may result in a sensor having a working electrode that can readily reduce available hydrogen peroxide and consequently have a lower electrode potential. Sensors designed to function with lower electrode potentials are typical embodiments of the invention because high electrode potentials in sensors of this type can result in a gas producing hydrolysis reaction which can destabilize the sensors (due to the disruption of sensor layers from gas bubbles produced by hydrolysis reactions). In addition, in sensor embodiments designed so that the counter electrode is coated with a very thin layer of an analyte sensing layer comprising an enzyme such as glucose oxidase or lactate oxidase, the hydrogen peroxide generated in the enzymatic reaction is very close to the reactive surface of the counter electrode. This can increase the overall efficiency of the sensor in a manner that allows for the production of compact sensor designs which include for example, counter electrodes with smaller reactive surfaces.

E. Permutations of Analyte Sensor Apparatus and Elements

As noted above, the invention disclosed herein has a number of embodiments such as apparatuses that include sensors in the constellation of elements. Such embodiments of the invention allow artisans to generate a variety of permutations of the apparatuses disclosed herein. As noted above, illustrative general embodiments of the apparatus disclosed herein, the sensor element include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of a sensor element of the invention is shown in FIG. 2. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 2 the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or mote adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, nontoxic biocompatible polymers such as polyimide, biocompatible solder masks, epoxy acrylate copolymers, or the like. Further, these coatings can be photo-imageable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize a separate reference element not formed on the sensor. The exposed electrodes and/or contact pads can also undergo secondary processing through the apertures 108, such as additional plating processing, to prepare the surfaces and/or strengthen the conductive regions.

An analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. Typically the sensor chemistry layer 110 is disposed on portions of a working electrode and a counter electrode that comprise a conductive layer. Some methods for generating the thin sensor chemistry layer 110 include spin coating processes, dip and dry processes, low shear spraying processes, ink-jet printing processes, silk screen processes and the like. Most typically the thin sensor chemistry layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. In certain embodiments of the invention, the analyte modulating layer comprises a hydrophilic comb-copolymer having a central chain and a plurality of side chains coupled to the central chain, wherein at least one side chain comprises a silicone moiety.

In some embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including an UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming an UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

The sensors of the invention can have any desired configuration, for example planar or cylindrical. The base layer 102 can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements and coating layers are continuously applied.

A general embodiment of the invention includes a sensor designed for implantation within a body that comprises a base layer, an analyte sensing layer disposed upon the base layer which includes a plurality of sensor elements, an enzyme layer (typically less than 2 microns in thickness) disposed upon the analyte sensing layer which coats all of the plurality of sensing elements on the conductive layer, and one or more coating layers. Typically the enzyme layer comprises glucose oxidase; typically in a substantially fixed ratio with a carrier protein. In a specific embodiment, the glucose oxidase and the carrier protein are distributed in a substantially uniform manner throughout the disposed enzyme layer. Typically the carrier protein comprises albumin, typically in an amount of about 5% by weight. As used herein, "albumin" refers to those albumin proteins typically used by artisans to stabilize polypeptide compositions such as human serum albumin, bovine serum albumin and the like. In some embodiments of the invention, a coating layer is an analyte contacting layer which is disposed on the sensor so as to regulate the amount of analyte that can contact the enzyme layer. In further embodiments, the sensor includes an adhesion promoter layer disposed between the enzyme layer and the analyte contacting layer; and, the enzyme layer is less than 1, 0.5, 0.25 or 0.1 microns in thickness.

Embodiments of the invention include a design where an analyte sensing layer is disposed upon a porous metallic and/or ceramic and/or polymeric matrix with this combination of elements functioning as an electrode in the sensor. A related embodiment of the invention is an electrochemical analyte sensor which includes a base layer, a conductive layer disposed upon the base layer that includes at least one working electrode and at least one counter electrode, an analyte sensing layer disposed upon the conductive layer, wherein the analyte sensing layer is less than 2 microns in thickness; and an analyte modulating layer that regulates the amount of analyte that contacts the enzyme layer, typically by limiting the amount of analyte that can diffuse through the layer and contact the analyte sensing layer. In certain embodiments of the invention, the analyte modulating layer comprises a hydrophilic comb-copolymer having a central chain and a plurality of side chains coupled to the central chain, wherein at least one side chain comprises a silicone moiety. In an optional embodiment of the invention, the working electrode and/or the coated surface of the working electrode is larger than counter electrode and/or the coated surface of the counter electrode. In some embodiments, the enzyme layer comprises glucose oxidase stabilized by coating it on the working electrode and the counter electrode in combination with a carrier protein in a fixed ratio. In one embodiment, this glucose oxidase enzyme layer substantially covers the conductive layer. Embodiments where the glucose oxidase enzyme layer is disposed in a uniform coating over the whole conductive layer are typical because they may avoid problems associated with sensors having multiple different coatings on a single layer such as the selective delamination of different coatings having different material properties. Typically, the sensor includes an adhesion promoting layer disposed between the enzyme layer and the analyte modulating layer.

A related embodiment of the invention includes an electrochemical analyte sensor having a base layer, a conductive layer disposed upon the base layer that includes at least one working electrode, at least one reference electrode and at least one counter electrode, an enzyme layer disposed upon the conductive layer, and an analyte modulating cover layer that regulates the amount of analyte that contacts the enzyme layer. In some embodiments, the enzyme layer is less than 2 microns in thickness and is coated on at least a portion of the working electrode, the reference electrode and the counter electrode. In an illustrative embodiment, the enzyme layer substantially covers the working electrode, the reference electrode and the counter electrode. Optionally, the enzyme layer comprises glucose oxidase in combination with a carrier protein (e.g. albumin) in a fixed ratio. Typically, the sensor includes an adhesion promoting layer disposed between the enzyme layer and the analyte modulating layer.

Yet another embodiment of the invention comprises a dual infusion set including a glucose sensor for implantation within a body which includes a base layer, a conductive layer disposed upon the base layer, an analyte sensing layer comprising glucose oxidase disposed upon the conductive layer, wherein the glucose oxidase is stabilized by combining it with albumin in a defined ratio and further wherein the glucose oxidase and the albumin are distributed in a substantially uniform manner throughout the disposed layer, and a glucose limiting layer that regulates the amount of glucose that diffuses through the glucose limiting layer and contacts the glucose oxidase layer. In some embodiments, the conductive layer includes a plurality of sensor elements including at least one working electrode and at least one counter electrode.

F. Analyte Sensor Apparatus Configurations

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

FIG. 2 provides a diagrammatic view of a typical analyte sensor configuration of the current invention. Certain sensor configurations are of a relatively flat "ribbon" type configuration that can be made with the analyte sensor apparatus. Such "ribbon" type configurations illustrate an advantage of the sensors disclosed herein that arises due to the spin coating of sensing enzymes such as glucose oxidase, a manufacturing step that produces extremely thin enzyme coatings that allow for the design and production of highly flexible sensor geometries. Such thin enzyme coated sensors provide further advantages such as allowing for a smaller sensor area while maintaining sensor sensitivity, a highly desirable feature for implantable devices (e.g. smaller devices are easier to implant). Consequently, sensor embodiments of the invention that utilize very thin analyte sensing layers that can be formed by processes such as spin coating can have a wider range of geometrical configurations (e.g. planar) than those sensors that utilize enzyme layers formed via processes such as electrodeposition.

Certain sensor configurations include multiple conductive elements such as multiple working, counter and reference electrodes. Advantages of such configurations include increased surface area which provides for greater sensor sensitivity. For example, one sensor configuration introduces a third working sensor. One obvious advantage of such a configuration is signal averaging of three sensors which increases sensor accuracy. Other advantages include the ability to measure multiple analytes. In particular, analyte sensor configurations that include electrodes in this arrangement (e.g. multiple working, counter and reference electrodes) can be incorporated into multiple analyte sensors. The measurement of multiple analytes such as oxygen, hydrogen peroxide, glucose, lactate, potassium, calcium, and any other physiologically relevant substance/analyte provides a number of advantages, for example the ability of such sensors to provide a linear response as well as ease in calibration and/or recalibration.

The analyte sensors of the invention can be coupled with other medical devices such as medication infusion pumps. In an illustrative variation of this scheme, replaceable analyte sensors of the invention can be coupled with other medical devices such as medication infusion pumps, for example by the use of a port couple to the medical device (e.g. a subcutaneous port with a locking electrical connection).

II. Illustrative Methods and Materials for Apparatuses of the Invention

A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods

A typical embodiment of the invention disclosed herein is a method of making a dual infusion set apparatus for implantation within a mammal by combining a base layer with one or more infusion elements (e.g. a catheter) and in addition, one or more sensor elements as well as elements that facilitate in vivo placement of these elements such as piercing members. Optionally, the sensor is made by a process comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including chemical vapor deposition, physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a sensor chemistry enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y.

(1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Subsequent to treatment of the sensor elements, one or more additional functional coatings or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as exact the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. Among the copolymers listed above, the dimethylsiloxane-bisphenol A carbonate copolymer which comprises 50-55 wt % of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane non-siloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, the cover layer that is added to the glucose sensors of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a sensor chemistry layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane cover layer to be disposed in direct contact with the sensor chemistry layer in the absence of an adhesion promoter layer.

An illustrative embodiment of the invention is a method of making a sensor by providing a base layer, forming a sensor layer on the base layer, spin coating an enzyme layer on the sensor layer and then forming an analyte contacting layer (e.g. an analyte modulating layer such as a glucose limiting membrane) on the sensor, wherein the analyte contacting layer regulates the amount of analyte that can contact the enzyme layer. In some methods, the enzyme layer is vapor crosslinked on the sensor layer. In a typical embodiment of the invention, the sensor layer is formed to include at least one working electrode and at least one counter electrode. In certain embodiments, the enzyme layer is formed on at least a portion of the working electrode and at least a portion of the counter electrode. Typically, the enzyme layer that is formed on the sensor layer is less than 2, 1, 0.5, 0.25 or 0.1 microns in thickness. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, the adhesion promoter layer is subjected to a curing process prior to the formation of the analyte contacting layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Methods for Using Analyte Sensor Apparatus of the Invention

A related embodiment of the invention is a method of sensing an analyte within the body of a mammal and infusing a therapeutic composition to that mammal, the method comprising implanting a dual infusion set embodiment disclosed herein in to the mammal and then both delivering fluid and sensing an alteration in current at the working electrode and correlating the alteration in current with the presence of the analyte, so that the analyte is sensed. Typically the analyte sensor is polarized anodically such that the working electrode where the alteration in current is sensed is an anode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Sets of the Invention

In another embodiment of the invention, a kit and/or sensor set, useful for the sensing an analyte and delivering a therapeutic compositions as is described above, is provided. The kit and/or sensor set typically comprises a container, a label and an apparatus as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds an apparatus having a base, an infusion element for infusing insulin, a sensing element or sensing blood glucose and piercing members for inserting the infusion and sensing elements in vivo. The kit can further include other materials desirable from a commercial and user standpoint, including elements or devices designed to facilitate the introduction of the sensor into the analyte environment, other buffers, diluents, filters, needles, syringes, and package inserts with instructions for use.

Various publication citations are referenced throughout the specification. In addition, certain text from related art is reproduced herein to more clearly delineate the various embodiments of the invention. The disclosures of all citations in the specification are expressly incorporated herein by reference.

The invention claimed is:

1. A method for inhibiting interference of an electrochemical glucose sensor that monitors glucose levels in a patient, wherein the interference is caused by a phenolic preservative present in an insulin infusate infused by an apparatus for supplying a fluid to a body of the patient, the method comprising supplying the fluid to the body of the patient using the apparatus comprising:
a base adapted to secure the apparatus to skin of the patient;
a first piercing member coupled to and extending from the base, wherein the first piercing member comprises at least one cannula for infusing the fluid to an infusion site,
a second piercing member coupled to and extending from the base and including the electrochemical sensor having a sensor electrode for determining the glucose levels of the patient at a sensor placement site,
infusion set tubing adapted to connect to the at least one cannula;
wherein:
the first and second piercing members are disposed on a hub that can operatively engage and disengage from the base;
the first and second piercing members are coupled to the base in an orientation such that when the first and second piercing members are inserted into the patient, a first perforation channel made by the first piercing member is not in operable contact with a second perforation channel made by the second piercing member such that the fluid infused to the infusion site cannot flow through the first perforation channel or the second perforation channel to the sensor; and
the first and second piercing members are coupled to the base in the orientation such that when the first and second piercing members are inserted into the patient, the sensor and the at least one cannula are separated by at least seven millimeters of tissue;

so that the interference is inhibited.

2. The method of claim 1, wherein the sensor comprises a plurality of layers including:

a glucose oxidase layer that detectably alters an electrical current at the electrode in a presence of glucose; and an analyte modulating layer that modulates diffusion of glucose therethrough.

3. The method of claim 1, wherein the first and second piercing members are inserted into separate in vivo environments.

4. The method of claim 1, further comprising a medication infusion pump adapted to connect to the infusion set tubing.

5. A method for inhibiting interference of an electrochemical sensor that monitors a body characteristic of a patient, wherein the interference is caused by an interferant present in an infusate infused by an apparatus for supplying a fluid to a body of the patient, the method comprising supplying the fluid to the body of the patient using the apparatus comprising:

a base adapted to secure the apparatus to skin of the patient;

a first piercing member coupled to and extending from the base, wherein the first piercing member comprises at least one cannula for infusing the fluid to an infusion site, a second piercing member coupled to and extending from the base and including the electrochemical sensor having a sensor electrode for determining the body characteristic of the patient at a sensor placement site, infusion set tubing adapted to connect to the at least one cannula;

wherein:

the first and second piercing members are disposed on a hub that can operatively engage and disengage from the base;

the first and second piercing members are coupled to the base in an orientation such that when the first and second piercing members are inserted into the patient, a first perforation channel made by the first piercing member is not in operable contact with a second perforation channel made by the second piercing member such that the fluid infused to the infusion site cannot flow through the first perforation channel or the second perforation channel to the sensor;

the first and second piercing members are coupled to the base in the orientation such that when the first and second piercing members are inserted into the patient, the sensor and the at least one cannula are separated by at least seven millimeters of tissue; and the first and second piercing members are coupled to the base in the orientation so that when the at least one cannula and the sensor are disposed in the patient, the at least one cannula and the sensor function to anchor the apparatus to the skin of the patient;

so that the interference is inhibited.

* * * * *